(12) United States Patent
Abouabdellah et al.

(10) Patent No.: US 8,394,787 B2
(45) Date of Patent: Mar. 12, 2013

(54) 7-AZA-SPIRO[3.5]NONANE-7-CARBOXYLATE DERIVATIVES, PREPARATION THEREOF AND THERAPEUTIC USE THEREOF

(75) Inventors: Ahmed Abouabdellah, Paris (FR); Nathalie Chereze, Paris (FR); Aude Fayol, Paris (FR); Alistair Lochead, Paris (FR); Mourad Saady, Paris (FR); Julien Vache, Paris (FR); Philippe Yaiche, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/320,199

(22) PCT Filed: May 11, 2010

(86) PCT No.: PCT/FR2010/050914
§ 371 (c)(1),
(2), (4) Date: Feb. 7, 2012

(87) PCT Pub. No.: WO2010/130945
PCT Pub. Date: Nov. 18, 2010

(65) Prior Publication Data
US 2012/0129830 A1    May 24, 2012

(30) Foreign Application Priority Data
May 12, 2009    (FR) .................... 09 02269

(51) Int. Cl.
| | |
|---|---|
| A61K 31/397 | (2006.01) |
| C07D 205/12 | (2006.01) |
| C07D 263/30 | (2006.01) |
| C07D 261/06 | (2006.01) |
| C07D 221/20 | (2006.01) |
| A61K 31/422 | (2006.01) |
| A61K 31/421 | (2006.01) |
| A61K 31/438 | (2006.01) |

(52) U.S. Cl. .................. 514/210.18; 514/278; 514/374; 514/378; 546/16; 548/236; 548/248; 548/953

(58) Field of Classification Search ............. 514/210.18, 514/278, 374, 378; 546/16; 548/236, 248, 548/953
See application file for complete search history.

(56) References Cited

U.S. PATENT DOCUMENTS
2004/0167224 A1    8/2004 Ozaki et al.

FOREIGN PATENT DOCUMENTS
| | | |
|---|---|---|
| WO | WO2005/090322 A1 | 9/2005 |
| WO | WO2005/090347 A1 | 9/2005 |
| WO | WO2006/006490 A1 | 1/2006 |

OTHER PUBLICATIONS

International Search Report dated Aug. 26, 2010 issued in PCT/FR2010/050914.
International Preliminary Report on Patentability dated Nov. 15, 2011 issued in PCT/FR2010/050914.

*Primary Examiner* — Rebecca Anderson
*Assistant Examiner* — Samantha Shterengarts
(74) *Attorney, Agent, or Firm* — Scully, Scott, Murphy & Presser, P.C.

(57) ABSTRACT

The invention relates to compounds of the general formula (I) where: $R_2$ is a hydrogen or fluorine atom or a hydroxyl, cyano, trifluoromethyl, $C_{1-6}$-alkyl, $C_{1-6}$-alkoxy, or $NR_8R_9$ group; m, n, o and p independently are a number from 0 to 3, provided that $m+n \leq 7$ and that $o+p \leq 7$; A is a covalent bond, an oxygen atom, a $C_{1-6}$-alkylene group or a —O—$C_{1-6}$-alkylene group in which the end that is an oxygen atom is bonded to the $R_1$ group and the end that is an alkylene group is bonded to the carbon of the bicyclic compound; $R_1$ is an optionally substituted aryl or heteroaryl group; $R_3$ is a hydrogen or fluorine atom or a $C_{1-6}$-alkyl or trifluoromethyl group; $R_4$ is an optionally substituted 5-membered heterocyclic compounds; wherein the compounds can be in the state of a base or an acid addition salt. The invention can be used in therapeutics.

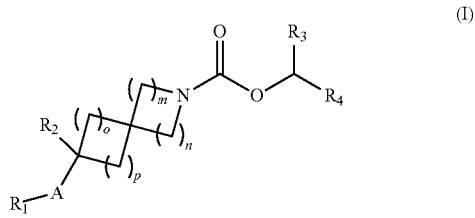

(I)

13 Claims, No Drawings

7-AZA-SPIRO[3.5]NONANE-7-CARBOXYLATE DERIVATIVES, PREPARATION THEREOF AND THERAPEUTIC USE THEREOF

The subject of the invention is 7-aza-spiro[3.5]nonane-7-carboxylate derivatives, the preparation thereof and the therapeutic use thereof.

There is still a need to find and develop products which inhibit the enzyme FAAH (Fatty Acid Amide Hydrolase). The compounds of the invention meet this purpose.

The compounds of the invention correspond to the general formula (I):

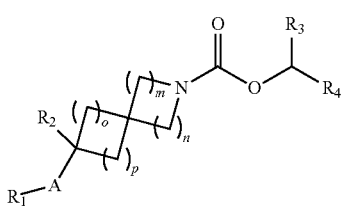

in which
$R_2$ represents a hydrogen or fluorine atom or a hydroxyl, cyano, trifluoromethyl, $C_{1-6}$-alkoxy or $NR_8R_9$ group;
m, n, o and p independently of one another represent a number ranging from 0 to 3;
it being understood that $2 \leq m+n \leq 5$ and that $2 \leq o+p \leq 5$;
A represents a covalent bond, an oxygen atom, a $C_{1-6}$-alkylene group or an —O—$C_{1-6}$-alkylene group in which the end represented by an oxygen atom is linked to the group $R_1$ and the end represented by an alkylene group is linked to the carbon of the bicyclic system;
$R_1$ represents a group $R_5$ optionally substituted with one or more groups $R_6$ and/or $R_7$;
$R_5$ represents a group selected from a phenyl, pyridinyl, pyridazinyl, pyrimidinyl, pyrazinyl, triazinyl, naphthalenyl, quinolinyl, isoquinolinyl, phthalazinyl, quinazolinyl, quinoxalinyl, cinnolinyl or naphthyrid-inyl group;
$R_6$ represents a halogen atom, a cyano, —$CH_2CN$, nitro, hydroxyl, $C_{1-6}$-alkyl, $C_{1-6}$-alkoxy, $C_{1-6}$-haloalkyl, $C_{1-6}$-haloalkoxy, $C_{1-6}$-halothioalkyl, $C_{3-7}$-cycloalkyl, $NR_8R_9$, $NR_8COR_9$, $NR_8CO_2R_9$, $NR_3SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O group;
$R_7$ represents a group selected from a phenyl, pyridinyl, pyridazinyl, pyrimidinyl, pyrazinyl or triazinyl group, the group or group(s) $R_7$ possibly being substituted with one or more groups $R_6$ which are identical to or different from one other;
$R_3$ represents, a hydrogen or fluorine atom, a $C_{1-6}$-alkyl group or a trifluoromethyl group;
$R_4$ represents a 5-membered heterocycle selected from a furanyl, pyrrolyl, thienyl, thiazolyl, isothiazolyl, oxazolyl, isoxazolyl, pyrazolyl, oxadiazolyl, thiadiazolyl, imidazolyl, triazolyl or tetrazoyl group; this heterocycle optionally being substituted with one or more substituents selected from a halogen atom, or a $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)$ ($C_{1-3}$-alkylene-$NR_{10}R_{11}$), $SO_2R_8$/$SO_2NR_8R_9$, or —O—($C_{1-3}$-alkylene)-O— group;
$R_8$ and $R_9$ independently of each other represent a hydrogen atom or a $C_{1-6}$-alkyl group;
or with the atom or atoms which bear them form,
in the case of $NR_8R_9$, a ring selected from the azetidine, pyrrolidine, piperidine, morpholine, thiomorpholine, azepine, oxazepine or piperazine rings, this ring possibly being substituted with a $C_{1-5}$-alkyl or benzyl group;
in the case of $NR_8COR_9$, a lactam ring; in the case of $NR_8CO_2R_9$, an oxazolidinone, oxazinone or oxazepinone ring; in the case of $NR_8SO_2R_9$, a sultam-ring; and in the case of $NR_8SO_2NR_8R_9$, a thiazolidine dioxide or thiadiazinane dioxide ring; and
$R_{10}$ and $R_{11}$ independently of one another represent a hydrogen atom or a $C_{1-6}$-alkyl group.

Among the compounds of general formula (I), a first subgroup of compounds is made up of compounds for which $R_2$ represents a hydrogen atom.

Among the compounds of general formula (I), a second subgroup of compounds is made up of compounds for which m, n, o and p have the value 1 or 2.

Among this subgroup, another group of compounds is made up of the compounds for which m and n have the value 1 or 2 and o and p have the value 1.

Among the compounds of general formula (I), a third subgroup of compounds is made up of compounds for which m, n, o and p have the value 1, or else p and o have the value 1 and n and m have the value 2, or else n, o and p have the value 1 and m has the value 2.

Among the compounds of general formula (I), a fourth subgroup of compounds is made up of compounds for which A represents an oxygen atom.

Among the compounds of general formula (I), a fifth subgroup of compounds is made up of compounds for which $R_1$ represents a group $R_5$, unsubstituted or substituted with one or more groups $R_6$ and/or $R_7$;
$R_5$ represents a phenyl, naphthalenyl or isoquinolinyl group;
$R_6$ represents a halogen atom, more particularly a fluorine or chlorine atom, or a $C_{1-6}$-haloalkyl, more particularly trifluoromethyl, group or a $C_{1-6}$-alkoxy group, more particularly an ethoxy group; and
$R_7$ represents a phenyl which may be substituted with one or more groups $R_6$ which are identical to or different from one another.

Among the compounds of general formula (I), a sixth subgroup of compounds is made up of compounds for which $R_1$ represents a group $R_5$ substituted with one or more groups $R_6$ and/or $R_7$;
$R_5$ represents a phenyl group;
$R_6$ represents a halogen atom, more particularly a fluorine or chlorine atom, or a $C_{1-6}$-haloalkyl, more particularly trifluoromethyl, group; and
$R_7$ represents a phenyl which may be substituted with one or more groups $R_6$ which are identical to or different from one another, selected from a halogen atom, more particularly a fluorine atom.

Among the compounds of general formula (I), an eighth subgroup of compounds is made up of compounds for which $R_1$ represents a group $R_5$ substituted with one or more groups $R_6$;
$R_5$ represents a naphthalen-2-yl group; and
$R_6$ represents a $C_{1-6}$-alkoxy group, more particularly an ethoxy group.

Among the compounds of general formula (I), a ninth subgroup of compounds is made up of compounds for which $R_1$ represents a group $R_5$ substituted with one or more groups $R_6$;
$R_5$ represents a naphthalen-1-yl group; and $R_6$ represents a halogen atom, more particularly a chlorine atom.

Among the compounds of general formula (I), a tenth subgroup of compounds is made up of compounds for which $R_1$ represents an unsubstituted group $R_5$ and $R_5$ represents an isoquinolin-7-yl group.

Among the compounds of general formula (I), an eleventh subgroup of compounds is made up of compounds for which $R_3$ represents a hydrogen atom.

Among the compounds of general formula (I), a twelfth subgroup of compounds is made up of compounds for which $R_4$ represents a group selected from a thiazolyl, a triazolyl, an oxazolyl or an isoxazolyl;
this group being unsubstituted or substituted with one or more $C_{1-6}$ alkyl or $CONR_8R_9$ groups;
$R_8$ and $R_9$ independently of one another represent a hydrogen atom or a $C_{1-6}$-alkyl group. More particularly, the $C_{1-6}$-alkyl group is a methyl.

Among the compounds of general formula (I), a thirteenth subgroup of compounds is made up of compounds for which $R_4$ represents a thiazol-4-yl group, this group being unsubstituted.

Among the compounds of general formula (I), a fourteenth subgroup of compounds is made up of compounds for which $R_4$ represents a thiazol-2-yl group, this group being substituted with one or more $CONR_8R_9$ groups;
$R_8$ and $R_9$ independently of one another represent a hydrogen atom or a $C_{1-6}$ alkyl group. More particularly, the $C_{1-6}$-alkyl group is a methyl.

Among the compounds of general formula (I), a fifteenth subgroup of compounds is made up of compounds for which $R_4$ represents an isoxazol-5-yl group;
this group being substituted with one or more $CONR_8R_9$ groups;
$R_8$ and $R_9$ independently of one another represent a hydrogen atom or a $C_{1-6}$-alkyl group. More particularly, the $C_{1-6}$-alkyl group is a methyl.

Among the compounds of general formula (I), a sixteenth subgroup of compounds is made up of compounds for which $R_4$ represents a group selected from any 1H-1,2,4-triazol-5-yl group; this group being substituted with one or more $C_{1-6}$-alkyl groups.

Among the compounds of general formula (I), a seventeenth subgroup of compounds is made up of compounds for which $R_4$ represents a group selected from any oxazol-2-yl; this group being substituted with one or more $CONR_8R_9$ groups;
$R_8$ and $R_9$ independently of one another represent a hydrogen atom or a $C_{1-6}$-alkyl group. More particularly, the $C_{1-6}$-alkyl group is a methyl.

Among the compounds of general formula (I), an eighteenth subgroup of compounds is made up of compounds of general formula (I) in which at the same time $R_1$ and/or $R_2$ and/or $R_3$ and/or $R_4$ and/or n and/or m and/or o and/or p and or A are as defined in the above groups.

Among the compounds of general formula (I), the following compounds can be cited (IUPAC nomenclature generated by the software AutoNom):
1. Thiazol-4-ylmethyl 2-(4-chlorophenoxy)-7-aza-spiro-[3.5]nonane-7-carboxylate.
2. 2-methyl-2H-[1,2,4]triazol-3-ylmethyl 2-(4-chlorophenoxy)-7-aza-spiro[3.5]nonane-7-carboxylate and the hydrochloride thereof.
3. 3-methylcarbamoyl-isoxazol-5-ylmethyl 2-(4-chlorophenoxy)-7-aza-spiro[3.5]nonane-7-carboxylate.
4. 3-carbamoyl-isoxazol-5-ylmethyl 2-(4-chlorophenoxy)-7-aza-spiro[3.5]nonane-7-carboxylate.
5. 3-methylcarbamoyl-isoxazol-5-ylmethyl 2-(3-trifluoromethylphenoxy)-7-aza-spiro[3.5]nonane-7-carboxylate.
6. 3-carbamoyl-isoxazol-5-ylmethyl 2-(3-trifluoromethylphenoxy)-7-aza-spiro[3.5]nonane-7-carboxylate.
7. 3-methylcarbamoyl-isoxazol-5-ylmethyl 2-(4'-fluorobiphenyl-3-yloxy)-7-aza-spiro[3.5]nonane-7-carboxylate.
8. 3-methylcarbamoyl-isoxazol-5-ylmethyl 2-(7-ethoxynaphthalen-2-yloxy)-7-aza-spiro[3.5]nonane-7-carboxylate.
9. 3-carbamoyl-isoxazol-5-ylmethyl 2-(3-trifluoromethylphenoxy)-6-aza-spiro[3.4]octane-6-carboxylate and the hydrochloride thereof (isomers I+II).
10. 3-carbamoyl-isoxazol-5-ylmethyl 2-(3-trifluoromethylphenoxy)-6-aza-spiro[3.4]octane-6-carboxylate (isomer I of compound No. 9).
11. 3-carbamoyl-isoxazol-5-ylmethyl 2-(3-trifluoromethylphenoxy)-6-aza-spiro[3.4]octane-6-carboxylate (isomer II of compound No. 9).
12. 3-carbamoyl-isoxazol-5-ylmethyl 2-(4'-fluorobiphenyl-3-yloxy)-7-aza-spiro[3.5]nonane-7-carboxylate.
13. 3-carbamoyl-isoxazol-5-ylmethyl 2-(7-ethoxynaphthalen-2-yloxy)-7-aza-spiro[3.5]nonane-7-carboxylate.
14. 4-carbamoyl-oxazol-2-ylmethyl 2-(3-trifluoromethylphenoxy)-6-aza-spiro[3.4]octane-6-carboxylate (isomers I+II).
15. 4-methylcarbamoyl-oxazol-2-ylmethyl 2-(3-trifluoromethylphenoxy)-6-aza-spiro[3.4]octane-6-carboxylate (isomers I+II).
16. 3-carbamoyl-isoxazol-5-ylmethyl 2-(4-chloronaphthalen-1-yloxy)-7-aza-spiro[3.5]nonane-7-carboxylate.
17. 3-methylcarbamoyl-isoxazol-5-ylmethyl 2-(4-chloronaphthalen-1-yloxy)-7-aza-spiro[3.5]nonane-7-carboxylate.
18. 3-carbamoyl-isoxazol-5-ylmethyl 2-(4'-fluorobiphenyl-4-yloxy)-7-aza-spiro[3.5]nonane-7-carboxylate.
19. 3-methylcarbamoyl-isoxazol-5-ylmethyl 2-(4'-fluorobiphenyl-4-yloxy)-7-aza-spiro[3.5]nonane-7-carboxylate.
20. 4-methylcarbamoyl-thiazol-2-ylmethyl 2-(4'-fluorobiphenyl-3-yloxy)-7-aza-spiro[3.5]nonane-7-carboxylate.
21. 3-methylcarbamoyl-isoxazol-5-ylmethyl 2-(isoquinolin-7-yloxy)-7-aza-spiro[3.5]nonane-7-carboxylate,
22. 3-methylcarbamoyl-isoxazol-5-ylmethyl 2-(4-chloro-3-fluorophenoxy)-7-aza-spiro[3.5]nonane-7-carboxylate.
23. 3-methylcarbamoyl-isoxazol-5-ylmethyl 6-(4-chloro-3-fluorophenoxy)-2-aza-spiro[3.3]heptane-2-carboxylate.
24. 3-carbamoyl-isoxazol-5-ylmethyl 6-(4-chloro-3-fluorophenoxy)-2-aza-spiro[3.3]heptane-2-carboxylate.
25. 3-methylcarbamoyl-isoxazol-5-ylmethyl 6-(4'-fluorobiphenyl-4-yloxy)-2-aza-spiro[3.3]heptane-2-carboxylate.
26. 3-carbamoyl-isoxazol-5-ylmethyl 2-(4-chloro-3-fluorophenoxy)-6-aza-spiro[3.4]octane-6-carboxylate (isomers I+II).
27. 3-methylcarbamoyl-isoxazol-5-ylmethyl 2-(4-chlorophenoxy)-6-aza-spiro[3,4]octane-6-carboxylate (isomers I+II).
28. 3-carbamoyl-isoxazol-5-ylmethyl 2-(4'-fluorobiphenyl-4-yloxy)-6-aza-spiro[3.4]octane-6-carboxylate (isomers I+II).
29. 3-methylcarbamoyl-isoxazol-5-ylmethyl 2-(4'-fluorobiphenyl-4-yloxy)-6-aza-spiro[3.4]octane-6-carboxylate (isomers I+II).
30. 3-carbamoyl-isoxazol-5-ylmethyl 2-(4-chloronaphthalen-1-yloxy)-6-aza-spiro[3.4]octane-6-carboxylate (isomers I+II).
31. 3-methylcarbamoyl-isoxazol-5-ylmethyl 2-(4-chloronaphthalen-1-yloxy)-6-aza-spiro[3.4]octane-6-carboxylate (isomers I+II).

32. 3-methylcarbamoyl-isoxazol-5-ylmethyl 2-(4'-fluorobiphenyl-4-yloxy)-6-aza-spiro[3.4]octane-6-carboxylate (isomer I of compound 29).
33. 3-methylcarbamoyl-isoxazol-5-ylmethyl 2-(4'-fluorobiphenyl-4-yloxy)-6-aza-spiro[3.4]octane-6-carboxylate (isomer II of compound 29).

The compounds of general formula (I) can contain one or more asymmetric carbons. They can exist in the form of enantiomers or diastereoisomers. The compounds of general formula (I) can also exist in the form of cis or trans stereoisomers. These stereoisomers, enantiomers and diastereoisomers, and mixtures thereof, including racemic mixtures, are part of the invention.

The compounds of formula (I) can exist in the state of bases or of acid addition salts. Such addition salts are part of the invention.

These salts are advantageously prepared with pharmaceutically acceptable acids, but the salts of other acids useful, for example, for the purification or the isolation of the compounds of formula (I) are also part of the invention.

In the context of the invention, the following meanings are understood:

$C_{t-z}$ where t and z can take values from 1 to 8, a carbon chain which can have from t to z carbon atoms, for example $C_{1-3}$, a carbon chain which can have from 1 to 3 carbon atoms;

alkyl, a saturated, linear or branched aliphatic group, for example a $C_{1-6}$-alkyl group represents a linear or branched carbon chain of 1 to 6 carbon atoms, more particularly a methyl, ethyl, propyl, isopropyl, butyl, isobutyl, tert-butyl, pentyl or hexyl;

alkylene, a divalent saturated, linear or branched, alkyl group, for example a $C_{1-3}$-alkylene group represents a divalent, linear or branched carbon chain of 1 to 3 carbon atoms, more particularly a methylene, ethylene, 1-methylethylene or propylene;

cycloalkyl, a cyclic alkyl group, for example a $C_{3-7}$-cycloalkyl group represents a cyclic carbon group of 3 to 7 carbon atoms, more particularly a cyclopropyl, cyclobutyl, cyclopentyl, cyclohexyl or cycloheptyl;

alkoxy, an —O-alkyl group with a saturated, linear or branched aliphatic chain;

thioalkyl, an —S-alkyl group with a saturated, linear or branched aliphatic chain;

haloalkyl, an alkyl group one or more hydrogen atoms whereof have been replaced by a halogen atom;

haloalkoxy, an alkoxy group one or more hydrogen atoms whereof have been replaced by a halogen atom;

halothioalkyl, a thioalkyl group one or more hydrogen atoms whereof have been replaced by a halogen atom;

halogen atom, a fluorine, chlorine, bromine or iodine;

TFA: trifluoroacetic acid;

ACM: acetonitrile.

The compounds of the invention can be prepared by different methods, illustrated by the following schemes. These methods, and the intermediate compounds used, are a subject of the present invention.

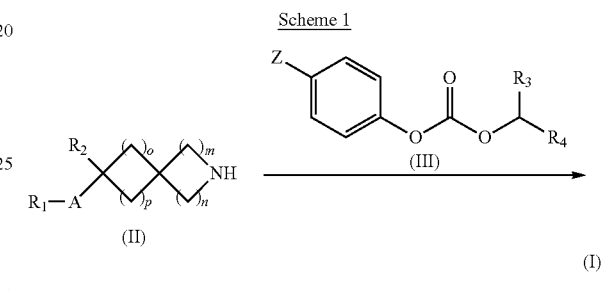

Scheme 1

Thus a first preparation method (scheme 1) consists in reacting an amine of general formula (II), in which A, $R_1$, $R_2$, m, n, o and p are as defined in the general formula (I) defined above, with a carbonate of general formula (III), in which Z represents a hydrogen atom or a nitro group, and $R_3$ and $R_4$ are as defined in the general formula (I) defined above, in presence of a base such as triethylamine, pyridine, N,N-dimethylaminopyridine or N,N-diisopropylethylamine, in a solvent such as toluene, acetonitrile or dichloroethane at a temperature lying between ambient temperature and the reflux temperature of the solvent.

Scheme 2

A second preparation method (scheme 2) for obtaining the compounds of general formula (I) in which A more particularly represents an oxygen atom or an —O—$C_{1-6}$-alkylene group, consists in reacting, in a first step, an alcohol of general formula (IIa), in which $R_2$, m, n, o and p are as defined in the general formula (I) defined above, G represents a part of the group A as defined in the general formula (I) namely either a covalent bond or the $C_{1-6}$-alkylene part of the —O—$C_{1-6}$-alkylene group and GP represents a protective group such as a Boo (tert-butyloxycarbonyl), Cbz (benzyloxycarbonyl), benzyl or benzhydryl;

either with an alcohol derivative of general formula (IV), in which $R_1$ is as defined above using the Mitsunobu reaction conditions (*Synthesis*, 1981, 1-28), or with a halogen derivative of general formula (IVa), in which $R_1$ is as defined above and X represents a fluorine, chlorine, bromine or iodine atom, using aromatic or heteroaromatic nucleophilic substitution, or O-arylation or Buchwald O-heteroarylation reactions, for example by means of a palladium- or copper-containing catalyst;

followed by a deprotection reaction, for example in presence of trifluoroacetic acid or a solution of hydrochloric acid in isopropanol or dioxan, to result in the amine of the general formula (IIb), in which G, $R_2$, m, n, o and p are as defined in the above amine of formula (IIa) and $R_1$ is as defined in the general formula (I) defined above. An alternative to the Mitsunobu reaction consists in reacting an alcohol derivative of general formula (IV) with the compounds of general formula (IIe) obtained by activation of the alcohol function of the compounds of general formula (IIa) by a tosylate group. The derivative of general formula (IIb) thus obtained is then transformed into a compound of general formula (I) by a condensation reaction with a carbonate of general formula (III) as defined above, under the conditions described above (Scheme 1).

An alternative for obtaining compounds of general formula (I) (Scheme 2) in which A more particularly represents an oxygen atom or an —O—$C_{1-6}$-alkylene group, consists in deprotecting an alcohol of general formula (IIa) as defined above, by a deprotection reaction as defined above in order to obtain an amino alcohol of general formula (IIc), then in reacting this amino alcohol of general formula (IIc), in which $R_2$, m, n, o and p are as defined in the general formula (I) defined above, and G represents a part of the group A as defined in the general formula (I) namely either a covalent bond or the $C_{1-6}$-alkylene part of the —O—$C_{1-6}$-alkylene group, with a carbonate of general formula (III) as defined above, under the conditions described above (Scheme 1), to result in the carbamate derivative of general formula (Ia), in which $R_2$, $R_3$, $R_4$, m, n, o and p are as defined in the general formula (I) defined above and G represents a part of the group A as defined in the general formula (I) namely either a covalent bond or the $C_{1-6}$-alkylene part of the —O—$C_{1-6}$-alkylene group. The carbamate derivative (Ia) thus obtained is then transformed into a compound of general formula (I) by the action of an alcohol of general formula $R_1OH$ (IV) as defined above, using the Mitsunobu reaction conditions or by the action of a halogenated derivative of general formula $R_1X$ (IVa) as defined above, using aromatic or heteroaromatic nucleophilic substitution, or O-arylation or Buchwald O-heteroarylation reactions, for example by means of a palladium- or copper-containing catalyst.

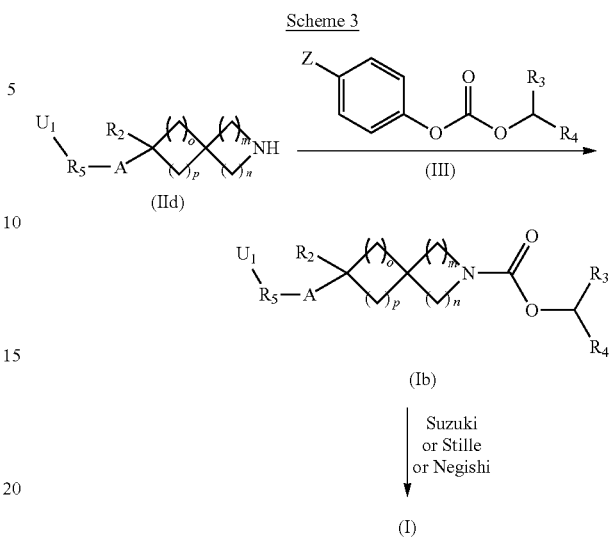

A third method (Scheme 3) was developed as regards the synthesis of compounds of general formula (I), in which $R_1$ represents a group $R_5$ substituted in particular with a group $R_6$ of the $C_{5-7}$-cycloalkyl or $C_{3-7}$-cycloalkyl-$C_{1-3}$-alkylene type, or with a group $R_7$ as defined in the general formula (I) defined above. Thus, the first stage consists in reacting an amine of general formula (IId), in which A, $R_2$, $R_5$, m, n, o and p are as defined in the general formula (I) defined above and $U_1$ represents a chlorine, bromine or iodine atom or a triflate group, with a carbonate of general formula (III) as defined above, under the conditions defined above (Scheme 1), to result in the carbamate derivative of general formula (Ib), in which A, $R_2$, $R_3$, $R_4$, $R_5$, m, n, o and p are as defined in the general formula (I) defined above and $U_1$ is as defined above. The coupling reaction catalysed by means of a transition metal such as palladium (0) is then performed on the key intermediate of general formula (Ib) as defined above, $U_1$ being in the position where it is desired to introduce the group $R_6$ or $R_7$ (Scheme 3):

either by a Suzuki type reaction, for example by means of an alkyl, cycloalkyl, aryl or heteroaryl boronic acid, or by a Stille type reaction, for example using an aryl or heteroaryl tri-alkyltin derivative or by a Negishi type reaction, for example using an alkyl, cycloalkyl, aryl or heteroaryl halide zincate derivative.

Another subject of the present invention relates to the compounds of formula (III)

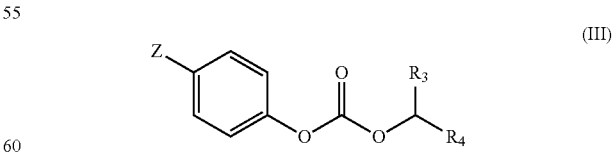

in which Z represents a hydrogen atom or a nitro group, $R_3$ is as defined in the formula (I) and $R_4$ represents a 4-(methylcarbamoyl)-oxazol-2-yl group.

Another subject of the present invention relates to the compounds of general formula (Ia):

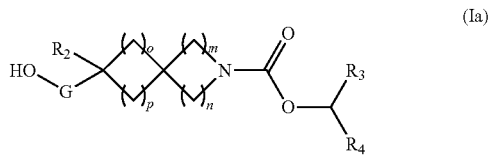

(Ia)

in which $R_2$, $R_3$, $R_4$, m, n, o and p are as defined in the general formula (I) and G represents a part of the group A as defined in the general formula (I) namely either a covalent bond or the $C_{1-6}$-alkylene part of the —O—$C_{1-6}$-alkylene group.

Among these compounds, thiazol-4-ylmethyl 2-hydroxy-7-aza-spiro[3.5]nonane-7-carboxylate may be cited.

Another subject of the present invention relates to the compounds of general formula (Ib):

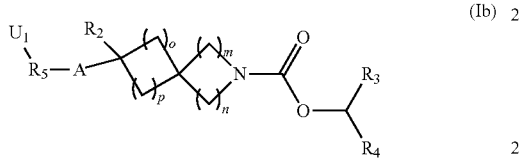

(Ib)

in which A, $R_2$, $R_3$, $R_4$, $R_5$, m, n, o and p are as defined in the general formula (I) according to claim 1 and $U_1$ represents a chlorine, bromine or iodine atom or a triflate group.

Another subject of the present invention relates to the compounds of general formula (II):

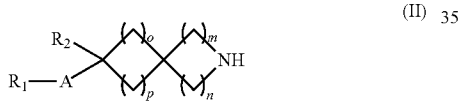

(II)

in which $R_1$, $R_2$, m, n, o and p are as defined in the general formula (I) and A represents an oxygen atom, it being given that $R_1$ is not a fluorophenyl group.

Among these compounds, the following can be cited:
2-(4-chlorophenoxy)-7-aza-spiro[3.5]nonane;
2-(4'-fluorobiphenyl-3-yloxy)-7-aza-spiro[3.5]nonane;
2-(4'-fluorobiphenyl-4-yloxy)-7-aza-spiro[3.5]nonane
($^1$H NMR (DMSO) δ (ppm): 8.80 (broad s, 2H), 7.65 (t, 2H); 7.60 (d, 2H); 7.30 (t, 2H); 6.95 (d, 2H); 4.80 (qt, 1H); 3.00 (broad d, 4H); 2.55 (m, 2H); 1.90 (m, 2H); 1.80 (dt, 4H));
2-(4-chloronaphthalen-1-yloxy)-7-aza-spiro[3.5]nonane;
2-(4-chloronaphthalen-1-yloxy)-6-aza-spiro[3.4]octane;
2-(3-trifluoromethylphenoxy)-6-aza-spiro[3.4]octane;
2-(4'-fluoro-biphenyl-4-yloxy)-6-aza-spiro[3.4]octane;
6-(4-chloro-3-fluorophenoxy)-2-aza-spiro[3.3]heptane;
6-(4'-fluorobiphenyl-4-yloxy)-2-aza-spiro[3.3]heptane;
2-(7-ethoxynaphthalen-2-yloxy)-7-aza-spiro[3.5]nonane
$^1$H NMR (DMSO) δ (ppm): 8.90 (broad s, 2H), 7.75 (d, 2H); 7.20 (s, 1H); 7.10 (s, 1H); 7.00 (d, 1H); 6.95 (d, 1H); 4.85 (qt, 1H); 4.15 (qd, 2H); 3.00 (broad d, 4H); 2.55 (m, 2H); 1.95 (m, 2H); 1.80 (dt, 4H); 1.40 (t, 3H));

6-(7-aza-spiro[3.5]non-2-yloxy)isoquinoline $^1$H NMR (DMSO) δ (ppm): 9.20 (s, 1H), 8.35 (d, 1H); 7.90 (d, 1H); 7.65 (d, 1H); 7.40 (t, 2H); 4.90 (qt, 1H); 2.65 (broad d, 4H); 2.50 (m, 2H); 1.85 (m, 2H); 1.55 (dt, 4H));

2-(4-chlorophenoxy)-6-aza-spiro[3.4]octane $^1$H NMR (DMSO) δ (ppm): 8.80 (broad s, 2H), 7.35 (d, 1H); 6.90 (t, 2H); 4.75 (qt, 1H); 3.20 (m, 4H); 2.60 (m, 2H); 2.15 (m, 2H); 2.00 (m, 2H)).

Another subject of the present invention relates to the compounds of general formula (IIa):

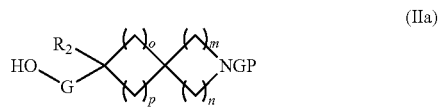

(IIa)

in which $R_2$ is as defined in the general formula (I), o and p represent 1, and m and n represent 1 or 2, but m and n do not together represent the value 2, G represents a part of the group A as defined in the general formula (I), namely either a covalent bond or the $C_{1-6}$-alkylene part of the —O—$C_{1-6}$-alkylene group, and GP represents a protective group such as a Boc (tert-butyloxycarbonyl), Cbz (benzyloxycarbonyl), benzyl or benzhydryl.

Among these compounds, the following can be cited: tert-butyl 2-hydroxy-6-aza-spiro[3.4]octane-6-carboxylate
$^1$H NMR (DMSO) δ (ppm): 4.7 (t, 1H); 4.1 (m, 1H); 3.2 (m, 4H); 2.2 (m, 2H); 1.8 (m, 4H); 1.4 (s, 9H)); tert-butyl 6-hydroxy-2-aza-spiro[3.3]heptane-2-carboxylate
($^1$H NMR (DMSO) δ (ppm): 5.00 (d, 1H); 3.95 (hex, 1H); 3.75 (d, 4H); 2.40 (m, 2H); 1.95 (m, 2H); 1.40 (s, 9H)).

Another subject of the present invention relates to the compounds of general formula (IIe):

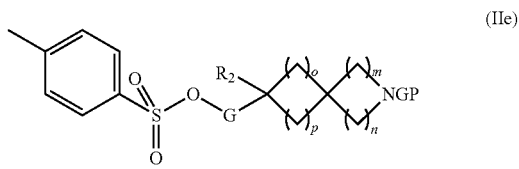

(IIe)

in which $R_2$ is as defined in the general formula (I), o and p represent 1, m and n represent 1 or 2, but m and n do not together represent the value 2, G represents a part of the group A as defined in the general formula (I), namely either a covalent bond or the $C_{1-6}$-alkylene part of the —O—$C_{1-6}$-alkylene group and GP represents a protective group such as a Hoc (tert-butyloxycarbonyl), Cbz (benzyloxycarbonyl), benzyl or benzhydryl.

Among these compounds, the following can be cited: tert-butyl 2-(toluene-4-sulphonyloxy)-6-aza-spiro[3.4]-octane-6-carboxylate
($^1$H NMR (DMSO) δ (ppm): 7.80 (d, 2H), 7.50 (d, 2H); 4.90 (m, 1H); 3.15 (m, 4H); 2.45 (s, 3H); 2.20 (m, 2H); 2.10 (m, 2H); 1.80 (t, 2H); 1.40 (s, 9H)); tert-butyl 2-(toluene-4-sulphonyloxy)-6-aza-spiro[3.4]-octane-6-carboxylate (isomer 2a)
($^1$H NMR (DMSO) δ (ppm): 7.80 (d, 2H), 7.50 (d, 2H); 4.90 (qt, 1H); 3.15 (m, 4H); 2.45 (s, 3H); 2.25 (t, 2H); 2.05 (t, 2H); 1.80 (m, 2H); 1.40 (s, 9H)); tert-butyl 2-(toluene-4-sulphonyloxy)-6-aza-spiro[3.4]-octane-6-carboxylate (isomer 2b)
($^1$H NMR (DMSO) δ (ppm): 7.80 (d, 2H), 7.50 (d, 2H); 4.90 (qt, 1H); 3.20 (m, 4H); 2.45 (s, 3H); 2.20 (t, 2H); 2.10 (t, 2H); 1.80 (m, 2H); 1.40 (s, 9H)).

The other compounds of general formulae (II), (IIa), (IIb), (IIc), (IId), (III), (IV) and (IVa) and the other reagents are commercially available or described in the literature, or else can be prepared by the methods which are described there and which are known by the person skilled in the art.

The examples that follow illustrate the preparation of some compounds of the invention. These examples are not limiting and only illustrate the invention. The microanalyses, the IR and NMR spectra and/or the LC-MS (Liquid Chromatography coupled to Mass Spectrometry) confirm the structures and the purities of the compounds obtained.

MP (° C.) represents the melting point in degrees Celsius.

$R_f$ indicates the retention time obtained by TLC (thin layer chromatography) analysis.

The numbers shown in brackets in the titles of the examples correspond to those in the first column in the tables below.

The IUPAC (International Union of Pure and Applied Chemistry) nomenclature was used for the naming of the compounds in the examples below.

Compound No. 9 is a mixture of isomers. Compound No. 10 is isomer I of compound No. 9 and compound No. 11 is isomer II of compound No. 9.

Compound No. 29 is a mixture of isomers. Compound No. 32 is isomer I of compound No. 29 and compound No. 33 is isomer II of compound No. 29.

Compounds 14, 15, 26, 27, 28, 30 and 31 are mixtures of isomers.

EXAMPLE 1

Compound No. 1

Thiazol-4-ylmethyl 2-(4-chlorophenoxy)-7-aza-spiro-[3.5]nonane-7-carboxylate 1.1 7-Aza-spiro[3.5]non-2-yl acetate, hydrobromide 0.800 g (2.91 mmoles) of benzyl 2-hydroxy-7-aza-spiro-[3.5]nonane-7-carboxylate (WO 9222550) is slowly added to 5 ml of a 5.7N solution of hydrobromic acid in acetic acid cooled to 0° C. After stirring for 1 hr at 0° C., 50 ml of diethyl ether are added and the medium is stirred for 1 hr. The precipitate formed is filtered on a fritted filter and copiously rinsed with diethyl ether. After drying overnight under vacuum at 80° C., 0.380 g of the expected product are obtained in the form of a white solid.

1.2 Thiazol-4-ylmethyl 2-acetoxy-7-aza-spiro[3.5]-nonane-7-carboxylate 0.280 g (1.06 mmoles) of 7-aza-spiro[3.5]non-2-yl acetate, hydrobromide, obtained in stage 1.1, is dissolved in 3 ml of methanol. 0.20 ml (1.17 mmoles) of N,N-diisopropylethylamine is added at ambient temperature. The medium is stirred for 3 minutes then 0.297 g (1.06 mmoles) of thiazole-4-ylmethyl (4-nitrophenyl)carbonate (WO 2008013834) in solution in 3 ml of dichloromethane is added. After stirring for 14 hrs at ambient temperature, the medium is diluted with dichloromethane and a 1N aqueous solution of caustic soda. After separation of the aqueous phase, the organic phase is washed twice with a 1N aqueous solution of caustic soda then three times with a saturated aqueous solution of ammonium chloride, dried over sodium sulphate, filtered and concentrated to dryness. 0.33 g of the expected product are obtained in the form of a powder, used as such in the following stage.

Melting point (° C.)=94-96° C.

$^1$H NMR (CDCl$_3$) δ (ppm): 8.85 (s, 1H), 7.40 (s, 1H); 5.35 (s, 2H); 5.10 (qt, 1H); 3.50 (m, 4H); 2.40 (m, 2H); 2.10 (s, 3H); 1.90 (m, 2H); 1.65 (m, 4H);

1.3 Thiazol-4-ylmethyl 2-hydroxy-7-aza-spiro[3.5]-nonane-7-carboxylate 0.267 g (0.82 mmole) of the thiazol-4-ylmethyl 2-acetoxy-7-aza-spiro[3.5]nonane-7-carboxylate obtained in stage 1.2 is dissolved in 2 ml of methanol then 0.5 ml of water and 0.114 g (0.82 mmole) of potassium carbonate are added. After stirring for 1 hr at ambient temperature, the medium is concentrated under vacuum then taken up in water. The aqueous solution is extracted twice with dichloromethane then the organic phases are combined, dried over sodium sulphate, filtered and concentrated to dryness. 0.222 g of the expected product are obtained in the form of a colour-less oil.

$^1$H NMR (CDCl$_3$) δ (ppm): 8.75 (s, 1H), 7.30 (s, 1H); 5.20 (s, 2H); 4.25 (qt, 1H); 3.35 (m, 4H); 2.20 (m, 2H); 1.65 (m, 2H); 1.45 (m, 4H).

1.4 Thiazol-4-ylmethyl 2-(4-chlorophenoxy)-7-aza-spiro-3.5]nonane-7-carboxylate

Under an inert atmosphere, 0.11 g (0.39 mmole) of thiazol-4-ylmethyl 2-hydroxy-7-aza-spiro[3.5]-nonane-7-carboxylate, obtained in stage 1.3, is dissolved in 4 ml of toluene. 0.160 g (0.61 mmole) of triphenylphosphine and 0.060 g (0.47 mmole) of 4-chlorophenol are added. The medium is cooled to 0° C. and a solution of 0.096 g (0.48 mmole) of diethylazodicarboxylate in 1 ml of toluene is added. The medium is stirred for 14 hrs at ambient temperature then concentrated under vacuum. The residue obtained is taken up in water and extracted twice with ethyl acetate. The combined organic phases are dried over sodium sulphate, filtered and concentrated under vacuum. The residue obtained is purified by silica gel chromatography eluting with a mixture of 50/50 to 80/20 of cyclohexane and ethyl acetate. 0.04 g of the expected product are obtained in the form of a solid.

Melting point (° C.): 86-88° C.

LC-MS: M-1-H=393

$^1$H NMR (CDCl$_3$) δ (ppm): 8.85 (s, 1H), 7.40 (s, 1H); 7.30 (t, 2H); 6.80 (d, 2H); 5.35 (s, 2H); 4.70 (qt, 1H); 3.35 (m, 4H); 2.45 (m, 2H); 2.00 (s, 2H); 1.65 (m, 4H).

EXAMPLE 2

Compound No. 2

2-Methyl-2H-[1,2,4]triazol-3-ylmethyl 2-(4-chlorophenoxy)-7-aza-spiro[3.5]nonane-7-carboxylate hydrochloride 2.1 Tert-butyl 2-(4-chlorophenoxy)-7-aza-spiro[3.5]-nonane-7-carboxylate Under an inert atmosphere, 0.60 g (2.49 mmoles) of tert-butyl 2-hydroxy-7-aza-spiro[3.5]-nonane-7-carboxylate (WO 2003084948) is dissolved in 25 ml of toluene. 1.024 g (3.90 mmoles) of triphenylphosphine and 0.384 g (2.98 mmoles) of 4-chlorophenol are added. The medium is cooled to 0° C., then a solution of 0.528 g (3.03 mmoles) of diethylazodicarboxylate in 3 ml of toluene is added. The medium is stirred for 14 hrs at ambient temperature then concentrated under vacuum. The residue obtained is taken up in a saturated aqueous solution of sodium carbonate and extracted twice with dichloromethane. The combined organic phases are washed once with a saturated aqueous solution of sodium chloride, dried over sodium sulphate, filtered and concentrated under vacuum. 0.874 g of a residue is obtained, which is used as such in the following stage.

2.2 2-(4-chlorophenoxy)-7-aza-spiro[3.5]-nonane 0.874 g (2.49 mmoles) of tert-butyl 2-(4-chlorophenoxy)-7-aza-spiro-[3.5]nonane-7-carboxylate, obtained in stage 2.1, is taken up in 5 ml of dioxan and 9.32 ml (37.29 mmoles) of a 4N solution of hydrochloric acid in dioxan are added slowly with stirring. After stirring for 3 hrs at ambient temperature, the medium is concentrated under vacuum and the residue is taken up in a 1N aqueous solution of hydrochloric acid. The aqueous phase is extracted twice with ethyl acetate then slowly basified to pH 10 by addition of 35% caustic soda solution. The aqueous phase is extracted three times with dichloromethane. These three organic extracts are combined, washed once with a saturated aqueous solution of sodium chloride, dried over sodium sulphate, filtered and concentrated under vacuum. 0.460 g of the expected product are obtained in the form of a yellow oil.

$^1$H NMR (DMSO) δ (ppm): 7.30 (d, 2H), 6.85 (d, 2H); 4.70 (qt, 1H); 2.65 (dt, 4H); 2.40 (m, 2H); 1.75 (m, 2H); 1.50 (dt, 4H).

2.3 2-Methyl-2H-[1,2,4]triazol-3-ylmethyl 2-(4-chlorophenoxy)-7-aza-spiro[3.5]nonane-7-carboxylate 0.100 g (0.40 mmole) of (2-methyl-2H-[1,2,4]triazol-3-yl) methanol and 0.15 ml (0.83 mmole) of N,N-diisopropylethylamine are dissolved in 4 ml of 1,2-dichloroethane. The medium is cooled to 0° C. then 0.08 g (0.40 mmole) of p-nitrophenyl chloroformate in solution in 2 ml of 1,2-dichloroethane is added. The mixture is stirred for 15 mins at ambient temperature then 0.100 g (0.40 mmole) of 2-(4-chlorophenoxy)-7-aza-spiro[3.5]-nonane, obtained in stage 2.2, is added. The mixture is heated at 60° C. for 15 hrs. After return to ambient temperature, the medium is diluted with a 1N aqueous solution of caustic soda, and the product is extracted with dichloromethane. The combined organic phases are then successively washed three times with a 1M aqueous solution of caustic soda, twice with a saturated aqueous solution of ammonium chloride and once with a saturated aqueous solution of sodium chloride, dried over sodium sulphate, filtered and evaporated to dryness. After purification on a silica gel column eluting with dichloromethane then with a 99/1/0.1 then 98/2/0.2 and 97/3/0.3 mixture of dichloromethane, methanol and 30% aqueous ammonia, 0.100 g of expected product are obtained in the form of a colourless oil which is taken up in a 5-6N solution of hydrochloric acid in propan-2-ol. The white solid formed is taken up in diethyl ether, filtered off and dried under vacuum. 0.80 g of the hydrochloride of the expected product are obtained in the form of a white powder.

Melting point (° C.): 163-165° C.
LC-MS: M+H=391
$^1$H NMR (DMSO) δ (ppm): 7.95 (s, 1H); 7.30 (d, 2H), 6.85 (d, 2H); 5.20 (s, 2H); 4.75 (qt, 1H); 3.90 (s, 3H); 3.35 (broad d, 4H); 2.45 (m, 2H); 1.80 (m, 2H); 1.55 (dt, 4H).

EXAMPLE 3

Compound No. 3

3-methylcarbamoyl-isoxazol-5-ylmethyl 2-(4-chlorophenoxy)-7-aza-spiro[3.5]nonane-7-carboxylate

3.1 3-ethoxycarbonyl-isoxazol-5-ylmethyl 2-(4-chlorophenoxy)-7-aza-spiro[3.5]nonane-7-carboxylate 0.172 g (1.00 mmole) of ethyl 5-hydroxymethyl-isoxazole-3-carboxylate and 0.33 ml (1.92 mmoles) of N,N-diisopropylethylamine are dissolved in 9 ml of 1,2-dichloroethane then cooled to 0° C. 0.184 g (0.91 mmole) of p-nitrophenyl chloroformate in solution in 2 ml of 1,2-dichloromethane are added. The mixture is stirred for 20 mins at ambient temperature, then 0.230 g (0.91 mmole) of 2-(4-chlorophenoxy)-7-aza-spiro[3.5]-nonane, obtained in stage 2.2, is added. The mixture is heated at 60° C. for 15 hrs. After return to ambient temperature, a 1N aqueous solution of caustic soda is added, and the product is extracted with dichloromethane. The combined organic phases are then successively washed three times with a 1N aqueous solution of caustic soda, twice with a saturated aqueous solution of ammonium chloride and once with a saturated aqueous solution of sodium chloride, dried over sodium sulphate, filtered and evaporated to dryness. 0.447 g of the expected product are obtained in the form of a colourless oil which is used as such in the following stage.

3.2 3-methylcarbamoyl-isoxazol-5-ylmethyl 2-(4-chlorophenoxy)-7-aza-spiro[3.5]nonane-7-carboxylate In a sealed tube, 0.180 g (0.40 mmole) of 3-ethoxycarbonyl-isoxazol-5-ylmethyl 2-(4-chlorophenoxy)-7-aza-spiro [3.5]nonane-7-carboxylate, obtained in stage 3.1, is dissolved in 5 ml of methanol. 0.5 ml (4.00 mmoles) of an 8N solution of methylamine in ethanol is added, then the medium, with the tube sealed, is heated at 60° C. with stirring for 3 hrs. After returning to ambient temperature, the medium is concentrated under vacuum and the residue obtained is chromatographed on silica gel preparative plates eluting with a 95/5/0.5 mixture of dichloromethane, methanol and 30% aqueous ammonia. 0.073 g of the expected product are thus obtained in the form of a white powder.

Melting point (° C.): 147-149° C.
LC-MS: M+H=434
$^1$H NMR (DMSO) δ (ppm): 8.85 (s, 1H); 7.35 (d, 2H), 6.90 (d, 2H); 6.80 (s, 1H); 5.25 (s, 2H); 4.75 (qt, 1H); 3.35 (broad d, 4H); 2.80 (s, 3H); 2.45 (m, 2H); 1.80 (m, 2H); 1.55 (dt, 4H).

EXAMPLE 4

Compound No. 4

3-carbamoyl-isoxazol-5-ylmethyl 2-(4-chlorophenoxy)-7-aza-spiro[3.5]nonane-7-carboxylate

4.1 3-carbamoyl-isoxazol-5-ylmethyl 2-(4-chlorophenoxy)-7-aza-spiro[3.5]nonane-7-carboxylate In a sealed tube, 0.190 g (0.42 mmole) of 3-ethoxycarbonyl-isoxazol-5-ylmethyl 2-(4-chlorophenoxy)-7-aza-spiro [3.5]nonane-7-carboxylate, obtained in stage 3.1, is dissolved in 5 ml of methanol. 0.91 ml (6.36 mmoles) of a 7N solution of ammonia in methanol is added, and the medium is heated at 50° C. for 15 hrs. After returning to ambient temperature, the medium is concentrated under vacuum and the residue obtained is chromatographed on silica gel preparative plates eluting with a 95/5/0.5 mixture of dichloromethane, methanol and 30% aqueous ammonia. An oil is obtained which crystallises in pentane. The solid obtained is filtered off and dried under vacuum at 60° C. 0.104 g of the expected product are obtained in the form of a white powder.

Melting point (° C.): 70-72° C.
LC-MS: M+H=420
$^1$H NMR (DMSO) δ (ppm): 8.15 (s, 1H); 7.85 (s, 1H); 7.30 (d, 2H), 6.90 (d, 2H); 6.80 (s, 1H); 5.25 (s, 2H); 4.75 (qt, 1H); 3.35 (broad d, 4H); 2.45 (t, 2H); 1.80 (t, 2H); 1.55 (d, 4H).

EXAMPLE 5

Compound No. 20

4-methylcarbamoyl-thiazol-2-ylmethyl 2-(4'-fluoro-biphenyl-3-yloxy)-7-aza-spiro[3.5]nonane-7-carboxylate 5.1 2-(4'-fluorobiphenyl-3-yloxy)-7-aza-spiro[3.5]-nonane The procedure described in Example 2 stages 2.1 and 2.2 is followed. From 0.500 g (2.07 mmoles) of tert-butyl 2-hydroxy-7-aza-spiro[3.5]-nonane-7-carboxylate (WO 2003084948), 0.468 g (2.49 mmoles) of 4'-fluorobiphenyl-3-ol, 0.440 g (2.53 mmoles) of diethyl azodicarboxylate, 0.853 g (3.25 mmoles) of triphenylphosphine and 7.77 ml of a 4N solution of hydrochloric acid in dioxan, 0.645 g of the expected product are obtained in the form of a wax used as such in the following stage.

5.2 Methyl 2-hydroxymethyl-thiazole-4-carboxylate 5.2.1 Ethyl 2-[(acetyloxy)methyl]1,3-thiazole-4-carboxylate 2.7 g (10.80 mmoles) of ethyl 2-(bromomethyl) thiazole-4-carboxylate are dissolved in 108 ml of acetonitrile. 2.225 g (22.67 mmoles) of potassium acetate are added and the mixture is stirred for 14 hrs at ambient temperature.
It is concentrated under reduced pressure. The residue obtained is taken up in a saturated aqueous solution of sodium chloride and extracted twice with dichloromethane. The combined organic phases are dried over sodium sulphate, filtered and concentrated to dryness. 2.347 g of the expected product are obtained in the form of a wax.
$^1$H NMR (CDCl$_3$) δ (ppm): 8.15 (s, 1H); 5.35 (s, 2H); 4.35 (qd, 2H); 2.10 (s, 3H); 1.35 (t, 3H).

5.2.2 Methyl 2-hydroxymethyl-thiazole-4-carboxylate 2.347 g (10.24 mmoles) of ethyl 2-acetoxymethyl-thiazole-4-carboxylate, obtained in stage 5.2.1, are dissolved in 100 ml of a 5/1 mixture of dichloromethane and methanol. 2.58 ml (11.26 mmoles) of a 4.37N solution of sodium methanolate in methanol are added and the medium is stirred for two hrs at ambient temperature before being concentrated under reduced pressure. The residue obtained is taken up in a saturated aqueous solution of sodium chloride and extracted three times with dichloromethane. The combined organic phases are washed once with a saturated aqueous solution of sodium chloride, dried over sodium sulphate, filtered and concentrated to dryness. The residue obtained is purified by silica gel chromatography eluting with a 98/2/0.2 mixture of dichloromethane, methanol and 30% aqueous ammonia. 0.92 g of the expected product are obtained in the form of a white powder.
Melting point (° C.): 158-160° C.
$^1$H NMR (CDCl$_3$) δ (ppm): 8.10 (s, 1H); 4.95 (s, 2H); 3.90 (s, 3H); 2.50 (broad s, 1H).

5.3 4-methoxycarbonyl-thiazol-2-ylmethyl 2-(4'-fluorobiphenyl-3-yloxy)-7-aza-spiro[3.5]nonane-7-carboxylate The procedure described in Example 2 stage 2.3 is followed. From 0.19 g (0.61 mmole) of 2-(4'-fluorobiphenyl-3-yloxy)-7-aza-spiro[3.5]nonane, obtained in stage 5.1, 0.127 g (0.73 mmole) of methyl 2-hydroxymethyl-thiazole-4-carboxylate, obtained in stage 5.2.2, 0.135 g (0.67 mmole) of para-nitrophenyl chloroformate and 0.265 ml (1.53 mmoles) of N,N-diisopropylethylamine and after silica gel chromatography eluting with a 99/1 mixture of dichloromethane and methanol, 0.161 g of the expected product are obtained in the form of a wax.
$^1$H NMR (CDCl$_3$) δ: 8.10 (s, 1H); 7.45 (t, 2H); 7.25 (t, 1H), 7.05 (m, 3H); 6.90 (d, 1H); 6.70 (d, 1H); 5.35 (s, 2H); 4.70 (qt, 1H); 3.90 (s, 3H); 3.40 (m, 4H); 2.35 (m, 2H); 1.95 (m, 2H); 1.60 (m, 4H).

5.4 4-methylcarbamoyl-thiazol-2-ylmethyl 2-(4'-fluorobiphenyl-3-yloxy)-7-aza-spiro[3.5]nonane-7-carboxylate In a sealed tube, 0.155 g (0.30 mmole) of 4-methoxycarbonyl-thiazol-2-ylmethyl 2-(4'-fluoro-biphenyl-3-yloxy)-7-aza-spiro[3.5]nonane-7-carboxylate, obtained in stage 5.3, is dissolved in 6 ml of ethanol. 1 ml (8.00 mmoles) of an 8N solution of methylamine in ethanol is added and the medium is stirred for 15 hrs at ambient temperature. After concentration of the medium under vacuum, the residue obtained is purified by silica gel chromatography eluting with dichloromethane, then with a 99/1/0.1 mixture of dichloromethane, methanol and 30% aqueous ammonia. A wax is obtained which crystallises in diisopropyl ether to give, after filtration and drying under vacuum at 60° C., 0.087 g of the expected product in the form of a white powder.
Melting point (° C.): 130-132° C.
LC-MS: M+H=510
$^1$H NMR (DMSO) δ (ppm): 8.35 (broad s, 1H); 8.25 (s, 1H); 7.70 (t, 2H); 7.35 (t, 1H); 7.30 (t, 2H); 7.20 (d, 1H); 7.05 (s, 1H); 6.85 (d, 1H); 5.35 (s, 2H); 4.90 (qt, 1H); 3.40 (broad d, 4H); 2.80 (s, 3H); 2.50 (m, 2H); 1.85 (m, 2H); 1.60 (dt, 4H).

EXAMPLE 6

Compound No. 17

3-methylcarbamoyl-isoxazol-5-ylmethyl 2-(4-chloronaphthalen-1-yloxy)-7-aza-spiro[3.5]nonane-7-carboxylate 6.1 3-methylcarbamoyl-isoxazol-5-ylmethyl 4-nitrophenyl carbonate 2.58 g (12.81 mmoles) of 4-nitrophenyl chloroformate are added in small portions to a solution of 2.00 g (12.81 mmoles) of 3-methylcarbamoyl-isoxazol-5-ylmethanol (commercial), 1.52 g (19.21 mmoles) of pyridine and 0.157 g (1.28 moles) of N,N-dimethylaminopyridine in 15 ml of dichloromethane, cooled to about 0° C. The medium is maintained with stirring for 1 hr at 0° C. then for 1 hr at ambient temperature. The precipitate formed is filtered off, then copiously rinsed with diisopropyl ether. After drying under vacuum at about 60° C., 2.6 g of pure product are obtained in the form of a white powder.

Melting point (° C.): 166-168° C.
¹H NMR (CDCl₃) δ (ppm): 8.40 (d, 2H); 7.50 (d, 2H); 7.0 (s, 1H); 6.90 (broad s, 1H); 5.50 (s, 2H); 3.10 (d, 3H).

6.2 2-(4-chloronaphthalen-1-yloxy)-7-aza-spiro[3.5]-nonane hydrochloride

Under an inert atmosphere, 1.00 g (4.14 mmoles) of tert-butyl 2-hydroxy-7-aza-spiro[3.5]-nonane-7-carboxylate (WO 2003084948) is dissolved in 41 ml of toluene. 1.250 g (4.77 mmoles) of triphenylphosphine and 0.888 g (4.97 mmoles) of 4-chloronaphthalen-1-ol (commercial) are added. The medium is cooled to 0° C. and a solution of 0.794 g (4.56 mmoles) of diethyl azodicarboxylate in 3 ml of toluene is added. The medium is stirred for 14 hrs at ambient temperature, then concentrated under vacuum. The residue obtained is taken up in a 1N aqueous solution of caustic soda and extracted twice with dichloromethane. The combined organic phases are washed once with a saturated aqueous solution of sodium chloride, dried over sodium sulphate, filtered and concentrated under vacuum. The crude residue is taken up in 20 ml of dichloromethane and 10 ml (40 mmoles) of a 4N solution of hydrochloric acid in dioxan are added slowly with stirring. After stirring for 3 hrs at ambient temperature, the medium is concentrated under vacuum and the residue is taken up in a 1N aqueous solution of hydrochloric acid. The aqueous phase is extracted twice with ethyl acetate then slowly basified to pH 10 by addition of 35% caustic soda solution. The aqueous phase is extracted three times with dichloromethane. These three organic extracts are combined, washed once with a saturated aqueous solution of sodium chloride, dried over sodium sulphate, filtered and concentrated under vacuum. The expected product is obtained in the form of a wax which is taken up in 2 ml of a 4N solution of hydrochloric acid in dioxan. The medium is diluted with diethyl ether and the precipitate formed is filtered off, rinsed with diethyl ether and dried under vacuum. 1.10 g of the hydrochloride of the expected product is obtained in the form of a white powder.

Melting point (° C.): 272-274° C.
LC-MS: M+H=302
¹H NMR (DMSO) δ (ppm): 8.75 (broad s, 2H); 8.25 (d, 1H); 8.15 (d, 1H), 7.75 (t, 1H); 7.65 (t, 1H); 7.60 (d, 1H); 6.80 (d, 1H); 4.95 (qt, 1H); 3.00 (broad d, 4H); 2.60 (m, 2H); 2.05 (m, 2H); 1.85 (dt, 4H).

6.3 3-methylcarbamoyl-isoxazol-5-ylmethyl 2-(4-chloronaphthalen-1-yloxy)-7-aza-spiro[3.5]nonane-7-carboxylate In a reaction tube, a mixture of 0.300 g (0.89 mmole) of 2-(4-chloronaphthalen-1-yloxy)-7-aza-spiro[3.5]-nonane hydrochloride, obtained in stage 6.2, 0.342 g (1.06 mmoles) of 3-methylcarbamoyl-isoxazol-5-ylmethyl 4-nitrophenyl carbonate, obtained in stage 6.1, 0.54 ml (3.10 mmoles) of N,N-diisopropylethylamine and 0.011 g (0.09 mmole) of N,N-dimethylaminopyridine is dissolved in 5 ml of 1,2-dichloroethane. The medium is then heated to 70° C. for 14 hrs. After return to ambient temperature, the medium is diluted with a 1N aqueous solution of caustic soda and extracted twice with dichloromethane. The combined organic phases are then successively washed twice with a 1N aqueous solution of caustic soda, once with a saturated aqueous solution of ammonium chloride and once with a saturated aqueous solution of sodium chloride. After drying over sodium sulphate, filtration and evaporation to dryness, the residue obtained is purified by silica gel chromatography eluting with dichloromethane, then with a 99/1/0.1 mixture of dichloromethane, methanol and 30% aqueous ammonia. 0.363 g of the expected product are obtained in the form of a white powder.

Melting point (° C.): 62-64° C.
LC-MS: M+H=484
¹H NMR (DMSO) δ (ppm): 8.70 (s, 2H); 8.25 (d, 1H); 8.15 (d, 1H), 7.75 (t, 1H); 7.65 (t, 1H); 7.60 (d, 1H); 6.80 (d, 2H); 5.25 (s, 2H); 4.95 (qt, 1H); 3.40 (broad d, 4H); 2.80 (s, 3H); 2.55 (m, 2H); 1.95 (m, 2H); 1.60 (dt, 4H).

EXAMPLE 7

Compound No. 30

3-carbamoyl-isoxazol-5-ylmethyl 2-(4-chloronaphthalen-1-yloxy)-6-aza-spiro[3.4]octane-6-carboxylate

7.1 Tert-butyl 2-hydroxy-6-aza-spiro[3.4]octane-6-carboxylate 0.89 g (23.57 mmoles) of sodium borohydride is added in portions at 0° C. to a solution of 3.54 g (15.71 mmoles) of tert-butyl 2-oxo-6-aza-spiro[3.4]octane-6-carboxylate (WO 9806720) diluted in 40 ml of methanol. The reaction mixture is stirred for 1 hr and 30 mins at ambient temperature. After evaporation of the solvent, water is added to the reaction mixture, the aqueous phase is separated, it is extracted several times with diethyl ether, and the combined organic phases are washed with a saturated aqueous solution of sodium chloride, they are dried over sodium sulphate and the filtrate is concentrated under reduced pressure. After evaporation of the solvent, 3.10 g of product are obtained in the form of a brown oil used as such in the following stage.

¹H NMR (DMSO) δ (ppm): 4.7 (t, 1H); 4.1 (m, 1H); 3.2 (m, 4H), 2.2 (m, 2H); 1.8 (m, 4H); 1.4 (s, 9H).

7.2 Tert-butyl 2-(4-chloronaphthalen-1-yloxy)-6-aza-spiro[3.4]octane-6-carboxylate The procedure described in Example 2, stage 2.1, is followed. From 3.50 g (15.40 mmoles) of tert-butyl 2-hydroxy-6-aza-spiro[3.4]octane-6-carboxylate, obtained in stage 7.1, 3.30 g (18.48 mmoles) of 4-chloronaphthalen-1-ol (commercial), 3.08 g (17.71 mmoles) of diethyl azodicarboxylate and 4.846 g (18.48 mmoles) of triphenylphosphine and after silica gel chromatography eluting with a 70/30, 60/40 then 50/50 mixture of cyclohexane and ethyl acetate, 6.14 g of the expected product are obtained in the form of an oil, used as such in the following stage.

7.3 2-(4-chloronaphthalen-1-yloxy)-6-aza-spiro[3.4]-octane trifluoroacetate 6.14 g of tert-butyl 2-(4-chloronaphthalen-1-yloxy)-6-aza-spiro[3.4]octane-6-carboxylate, obtained in stage 7.2, are dissolved in 100 ml of dichloromethane. The medium is cooled to 0° C. then 20 ml of trifluoroacetic acid are added slowly. After stirring for 2 hrs at ambient temperature, the medium is diluted with 100 ml of toluene and concentrated under vacuum. The residue obtained is taken up in diethyl ether to give a powder which is filtered off, rinsed with diethyl ether and dried under vacuum. 4.19 g of the expected product are obtained in the form of a pink powder.

Melting point (° C.): 129-131° C.
¹H NMR (DMSO) δ (ppm): 8.85 (broad s, 2H); 8.25, (d, 1H); 8.15 (d, 1H), 7.75 (t, 1H); 7.65 (t, 1H); 7.60 (d, 1H); 6.85

(dd, 1H); 5.00 (qt, 1H); 3.25 (m, 4H); 2.75 (m, 1H); 2.65 (m, 1H); 2.30 (m, 2H); 2.10 (m, 2H).

7.4 3-carbamoyl-isoxazol-5-ylmethyl 4-nitrophenyl carbonate 2.84 g (14.07 mmoles) of 4-nitrophenyl chloroformate are added in small portions to a solution of 2.0 g (14.07 mmoles) of 3-methylcarbamoyl-isoxazol-5-yl-methanol (commercial), 1.71 ml (21.11 mmoles) of pyridine and 0.17 g (1.41 moles) of N,N-dimethylaminopyridine in 15 ml of dichloromethane, cooled to about 0° C. The medium is maintained with stirring for 1 hr at 0° C. then for 1 hr at ambient temperature. The precipitate formed is filtered off then copiously rinsed with diisopropyl ether. After drying under vacuum at about 60° C., 3.12 g of the expected product are obtained in the form of a white solid used as such in the following stage.

Melting point (° C.) 143-145° C.
$^1$H NMR (DMSO) δ (ppm): 8.40 (d, 2H); 8.25 (broad s, 1H); 7.90 (broad s, 1H), 7.65 (d, 2H); 7.0 (s, 1H); 5.50 (s, 2H).

7.5 3-carbamoyl-isoxazol-5-ylmethyl 2-(4-chloronaphthalen-1-yloxy)-6-aza-spiro[3.4]octane-6-carboxylate In a reaction tube, a mixture of 1.000 g (2.49 mmoles) of 2-(4-chloronaphthalen-1-yloxy)-6-aza-spiro[3.4]-octane trifluoroacetate, obtained in stage 7.3, 0.841 g (2.74 mmoles) of 3-methylcarbamoyl-isoxazol-5-ylmethyl 4-nitrophenyl carbonate, obtained in stage 7.4, 1.30 ml (7.47 mmoles) of N,N-diisopropylethylamine and 0.032 g (0.25 mmole) of N,N-dimethylaminopyridine is dissolved in 8 ml of 1,2-dichloroethane. The medium, with the tube sealed, is heated to 70° C. with stirring for 14 hrs. After return to ambient temperature, the medium is diluted with a 1N aqueous solution of caustic soda and extracted twice with dichloromethane. The combined organic phases are then successively washed twice with a 1N aqueous solution of caustic soda, once with a saturated aqueous solution of ammonium chloride and once with a saturated aqueous solution of sodium chloride. After drying over sodium sulphate, filtration and evaporation to dryness, the residue is purified by silica gel chromatography eluting with a 99/1/0.1, then 98/2/0.2 mixture of dichloromethane, methanol and 30% aqueous ammonia. 1.15 g of the expected product are obtained in the form of a white powder.

Melting point (° C.): 149-150° C.
LC-MS: M+H=456
$^1$H NMR (DMSO) δ (ppm): 8.25 (d, 1H); 8.15 (d, 2H), 7.85 (broad s, 1H); 7.75 (t, 1H); 7.65 (t, 1H); 7.55 (d, 1H); 6.85 (d, 1H); 6.80 (s, 1H); 5.25 (d, 2H); 5.00 (m, 1H); 3.40 (m, 4H); 2.65 (m, 2H); 2.20 (m, 2H); 2.00 (m, 2H).

EXAMPLE 8

Compound Nos. 10 and 11

3-carbamoyl-isoxazol-5-ylmethyl 2-(3-trifluoromethylphenoxy)-6-aza-spiro[3.4]octane-6-carboxylate (isomers I and II)

8.1 Tert-butyl 2-(3-trifluoromethylphenoxy)-6-aza-spiro[3.4]octane-6-carboxylate (isomers 1a and 1b)

0.910 g (4.00 mmoles) of tert-butyl 2-hydroxy-6-aza-spiro [3.4]octane-6-carboxylate, obtained in stage 7.1, is dissolved in 14 ml of dimethylformamide. 0.240 g (6.01 mmoles) of sodium hydride is added in portions, then 0.821 g (5.00 mmoles) of 1-fluoro-3-trifluoromethylbenzene (commercial) is added to the medium. After heating for 14 hrs at 90° C., the medium is allowed to return to ambient temperature then diluted in water and ethyl acetate. After decantation and separation, the aqueous phase is extracted a second time with ethyl acetate, then the combined organic phases are washed twice with water and once with a saturated aqueous solution of sodium chloride, dried over sodium sulphate and concentrated to dryness. 1.28 g of the expected isomers 1a and 1b is obtained in the form of an oil. 0.130 g (0.35 mmole) of the mixture of isomers is separated by chromatography on preparative silica gel plates eluting with a 70/30 mixture of cyclohexane and ethyl acetate.

0.042 g of the isomer 1a ($R_f$=0.55) and 0.045 g of the isomer 1b ($R_f$=0.65) are thus obtained in the form of colourless oils.

Isomer 1a
$R_f$=0.55 (ethyl acetate/cyclohexane: 70/30)
$^1$H NMR (DMSO) δ (ppm): 7.55 (t, 1H); 7.30 (d, 1H), 7.20 (d, 1H); 7.15 (s, 1H); 4.90 (qt, 1H); 3.35 (d, 2H); 3.25 (m, 2H); 2.55 (m, 2H); 2.05 (m, 2H); 1.90 (m, 2H); 1.45 (s, 9H).

Isomer 1b
$R_f$=0.65 (ethyl acetate/cyclohexane: 70/30)
$^1$H NMR (DMSO) δ (ppm): 7.55 (t, 1H); 7.30 (d, 1H), 7.20 (d, 1H); 7.15 (s, 1H); 4.85 (qt, 1H); 3.35-3.20 (m, 4H); 2.50 (m, 2H); 2.10 (m, 2H); 1.95 (m, 2H); 1.40 (s, 9H).

8.2 2-(3-trifluoromethylphenoxy)-6-aza-spiro[3.4] octane hydrochloride

8.2a 2-(3-trifluoromethylphenoxy)-6-aza-spiro[3.4]-octane hydrochloride (obtained from isomer 1a)

0.042 g (0.11 mmole) of tert-butyl 2-(3-trifluoromethylphenoxy)-6-aza-spiro[3.4]octane-6-carboxylate, isomer 1a, obtained in stage 8.1, is taken up in 3 ml of dioxan and 0.43 ml (1.71 mmoles) of a 4N solution of hydrochloric acid in dioxan is added slowly with stirring. After stirring for 14 hrs at ambient temperature, the medium is concentrated to dryness under reduced pressure. 0.035 g of the hydrochloride of the expected product is obtained in the form of a yellow oil.

8.2b 2-(3-trifluoromethylphenoxy)-6-aza-spiro[3.4]-octane hydrochloride (obtained from isomer 1b)

0.045 g (0.12 mmole) of tert-butyl 2-(3-trifluoromethylphenoxy)-6-aza-spiro[3.4]octane-6-carboxylate, isomer 1b, obtained in stage 8.1, is taken up in 3 ml of dioxan and 0.45 ml (1.82 mmoles) of a 4N solution of hydrochloric acid in dioxan is added slowly with stirring. After stirring for 14 hrs at ambient temperature, the medium is concentrated to dryness under reduced pressure. 0.037 g of the hydrochloride of the expected product is obtained in the form of a yellow oil.

8.3 3-carbamoyl-isoxazol-5-ylmethyl 2-(3-trifluoromethylphenoxy)-6-aza-spiro[3.4]octane-6-carboxylate

8.3a 3-carbamoyl-isoxazol-5-ylmethyl 2-(3-trifluoromethylphenoxy)-6-aza-spiro[3.4]octane-6-carboxylate (isomer I) (compound No. 10)

The procedure described in Example 6, stage 6.3, is followed. From 0.035 g (0.11 mmole) of 2-(3-trifluoromethylphenoxy)-6-aza-spiro[3.4]-octane hydrochloride, obtained in stage 8.2a, 0.042 g (0.14 mmole) of 3-carbamoyl-isoxazol- 5-ylmethyl 4-nitrophenyl carbonate, obtained in stage 7.4, 0.060 ml (0.34 mmole) of N,N-diisopropylethylamine and 0.007 g (0.06 mmole) of N,N-dimethylaminopyridine, and after purification by chromatography on preparative silica gel plates eluting with a 90/10/1 mixture of dichloromethane, methanol and 30% aqueous ammonia, a colourless oil is obtained which crystallises in pentane. After filtration and drying under vacuum at 60° C., 0.050 g of the expected product is obtained in the form of a white powder.

LC-MS: M+H=440

Melting point (° C.): 97-99° C.

$^1$H NMR (DMSO) δ (ppm): 8.15 (s, 1H); 7.85 (s, 1H); 7.55 (t, 1H); 7.30 (d, 1H), 7.20 (d, 1H); 7.15 (s, 1H); 6.85 (d, 1H); 5.25 (s, 2H); 4.90 (qt, 1H); 3.45 (s, 2H); 3.30 (m, 2H); 2.55 (m, 2H); 2.05 (m, 2H); 1.95 (m, 2H).

8.3b 3-carbamoyl-isoxazol-5-ylmethyl 2-(3-trifluoromethylphenoxy)-6-aza-spiro[3.4]octane-6-carboxylate (isomer II) (compound No. 11)

The procedure described in Example 6, stage 6.3, is followed. From 0.037 g (0.12 mmole) of 2-(3-trifluoromethylphenoxy)-6-aza-spiro[3.4]-octane hydrochloride, obtained in stage 8.2b, 0.042 g (0.14 mmole) of 3-carbamoyl-isoxazol-5-ylmethyl 4-nitrophenyl carbonate, obtained in stage 7.4, 0.060 ml (0.36 mmole) of N,N-diisopropylethylamine and 0.007 g (0.06 mmole) of N,N-dimethylaminopyridine, and after purification by chromatography on preparative silica gel plates eluting with a 90/10/1 mixture of dichloromethane, methanol and 30% aqueous ammonia, a colourless oil is obtained which crystallises in pentane. After filtration of the solid and drying under vacuum at 60° C., 0.029 g of the expected product is obtained in the form of a wax.

LC-MS: M+H=440

$^1$H NMR (DMSO) δ (ppm): 8.10 (s, 1H); 7.85 (s, 1H); 7.55 (t, 1H); 7.30 (d, 1H), 7.20 (d, 1H); 7.15 (s, 1H); 6.80 (s, 1H); 5.25 (s, 2H); 4.85 (qt, 1H); 3.45-3.25 (m, 5H); 2.50 (m, 2H); 2.10 (m, 2H); 1.95 (m, 2H).

EXAMPLE 9

Compound Nos. 32 and 33

3-methylcarbamoyl-isoxazol-5-ylmethyl 2-(4'-fluorobiphenyl-4-yloxy)-6-aza-spiro[3.4]octane-6-carboxylate (isomers I and II)

9.1 Tert-butyl 2-(toluene-4-sulphonyloxy)-6-aza-spiro-[3.4]octane-6-carboxylate (isomers 2a and 2b)

10.00 g (43.99 mmoles) of tert-butyl 2-hydroxy-6-aza-spiro-[3.4]octane-6-carboxylate, obtained in stage 7.1, and 9.15 ml (65.98 mmoles) of triethylamine are dissolved in 400 ml of dichloromethane and 13.07 g (65.98 mmoles) of tosyl chloride are added. After stirring for 14 hrs at ambient temperature, the medium is extracted once with a saturated aqueous solution of ammonium chloride then once with a saturated aqueous solution of sodium chloride, dried over sodium sulphate, filtered and concentrated under reduced pressure. The residue obtained is purified by silica gel chromatography eluting with cyclohexane, then with a 95/5 mixture of cyclohexane and ethyl acetate. 11.9 g of expected product are obtained in the form of an oil.

LC-MS: M+H=382

$^1$H NMR (DMSO) δ (ppm): 7.80 (d, 2H); 7.50 (d, 2H); 4.90 (m, 1H); 3.15 (m, 4H); 2.45 (s, 3H); 2.20 (m, 2H); 2.10 (m, 2H); 1.80 (t, 2H); 1.40 (s, 9H).

11.5 g (3.01 mmoles) of tert-butyl 2-(toluene-4-sulphonyloxy)-6-aza-spiro-[3.4]octane-6-carboxylate, obtained in stage 9.1, are separated by preparative chiral chromatography (Macherey-Nagel Nucleosil 50-10/50×220 mm) eluting with a 13/87 mixture of ethyl acetate and cyclohexane, to give 5.15 g of isomer 2a and 4.69 g of isomer 2b in the form of white powders.

Isomer 2a $T_r$=33 mins

Melting point (° C.): 83.7° C.

LC-MS: M+H=382

$^1$H NMR (DMSO) δ (ppm) 7.80 (d, 2H); 7.50 (d, 2H); 4.90 (qt, 1H); 3.15 (m, 4H); 2.45 (s, 3H); 2.25 (t, 2H); 2.05 (t, 2H); 1.80 (m, 2H); 1.40 (s, 9H).

Isomer 2b $T_r$=43 mins

Melting point (° C.): 94.9° C.

LC-MS: M+H=382

$^1$H NMR (DMSO) δ (ppm): 7.80 (d, 2H); 7.50 (d, 2H); 4.90 (qt, 1H); 3.20 (m, 4H); 2.45 (s, 3H); 2.20 (t, 2H); 2.10 (t, 2H); 1.80 (m, 2H); 1.40 (s, 9H).

9.2 Tert-butyl 2-(4'-fluorobiphenyl-4-yloxy)-6-aza-spiro[3.4]octane-6-carboxylate

9.2a Tert-butyl 2-(4'-fluorobiphenyl-4-yloxy)-6-aza-spiro[3.4]octane-6-carboxylate (obtained from the isomer 2a)

0.542 g (2.88 mmoles) of 4'-fluorobiphenyl-4-ol, 0.362 g (2.62 mmoles) of potassium carbonate and 0.693 g (2.62 mmoles) of 18-crown-6 are dissolved in 26 ml of N,N-dimethylformamide. The medium is heated to 80° C. with stirring then 1.00 g (2.62 mmoles) of the tert-butyl 2-(toluene-4-sulphonyloxy)-6-aza-spiro[3.4]-octane-6-carboxylate, isomer 2a, obtained in stage 9.1, in solution in 4 ml of N,N-dimethylformamide, is added drop by drop. After stirring for 14 hrs at 80° C., the medium is allowed to return to ambient temperature, then concentrated to dryness under reduced pressure. The residue is taken up in dichloromethane and a 1N aqueous solution of caustic soda. After decantation, the aqueous phase is separated and re-extracted twice with dichloromethane. The combined organic phases are washed with a saturated aqueous solution of sodium chloride, dried over sodium sulphate and concentrated under reduced pressure. The residue obtained is purified by silica gel chromatography eluting with a 90/10 mixture of cyclohexane and ethyl acetate. 0.80 g of the expected product are obtained in the form of a powder.

Melting point (° C.): 132-133° C.

LC-MS: M+H=398

$^1$H NMR (DMSO) δ (ppm): 7.65 (t, 2H); 7.55 (d, 2H); 7.25 (t, 2H); 6.95 (d, 2H); 4.80 (qt, 1H); 3.25 (m, 4H); 2.50 (m, 2H); 2.15 (m, 2H); 1.95 (m, 2H); 1.40 (s, 9H).

9.2b Tert-butyl 2-(4'-fluorobiphenyl-4-yloxy)-6-aza-spiro[3.4]octane-6-carboxylate (obtained from the isomer 2b)

The procedure described in Example 9, stage 9.2a, is followed. From 1.2 g (3.15 mmoles) of tert-butyl 2-(toluene-4-sulphonyloxy)-6-aza-spiro[3.4]-octane-6-carboxylate, isomer 2b, obtained in stage 9.1, 0.622 g (3.30 mmoles) of 4'-fluoro-biphenyl-4-ol, 0.435 g (3.15 mmoles) of potassium carbonate and 0.831 g (3.15 mmoles) of 18-crown-6, and after purification by silica gel chromatography eluting with a 90/10 mixture of cyclohexane and ethyl acetate, 0.860 g of the expected product are obtained in the form of a wax used as such in the following stage.

$^1$H NMR (DMSO) δ (ppm): 7.65 (t, 2H); 7.55 (d, 2H); 7.25 (t, 2H); 6.95 (d, 2H); 4.85 (qt, 1H); 3.30 (m, 2H); 3.25 (m, 2H); 2.55 (m, 2H); 2.05 (m, 2H); 1.90 (m, 2H); 1.40 (s, 9H).

9.3 2-(4'-fluorobiphenyl-4-yloxy)-6-aza-spiro[3.4]-octane hydrochloride

9.3a 2-(4'-fluorobiphenyl-4-yloxy)-6-aza-spiro[3.4]-octane hydrochloride (obtained from isomer 2a)

1.000 g (2.52 mmoles) of tert-butyl 2-(4'-fluoro-biphenyl-4-yloxy)-6-aza-spiro[3.4]-octane-6-carboxylate, obtained in stage 9.2a from isomer 2a, is dissolved in 8 ml of dioxan and 6.29 ml (25.16 mmoles) of a 4N solution of hydrochloric acid in dioxan are added slowly with stirring. After stirring for 4 hrs at ambient temperature, the medium is concentrated to dryness under reduced pressure and the residue obtained taken up in diethyl ether. After stirring for 2 hrs, the suspended solid is filtered off, copiously rinsed with diethyl ether and dried under vacuum. 0.690 g of the expected product is obtained in the form of a white powder.

Melting point (° C.): 227-229° C.
LC-MS: M+H=298
$^1$H NMR (DMSO) δ (ppm): 9.10 (broad s, 2H); 7.65 (t, 2H); 7.60 (d, 2H); 7.25 (t, 2H); 6.95 (d, 2H); 4.80 (qt, 1H); 3.20 (m, 4H); 2.55 (m, 2H); 2.20 (m, 2H); 2.05 (m, 2H).

9.3b 2-(4'-fluorobiphenyl-4-yloxy)-6-aza-spiro[3.4]-octane hydrochloride (obtained from isomer 2b)

The procedure described in Example 9, stage 9.3a is followed. From 0.860 g (2.16 mmoles) of tert-butyl 2-(4'-fluorobiphenyl-4-yloxy)-6-aza-spiro[3.4]-octane-6-carboxylate, obtained in stage 9.2b from isomer 2b, and 15 ml (60.00 mmoles) of a 4N solution of hydrochloric acid in dioxan, 0.545 g of the expected product is obtained in the form of a white powder.

Melting point (° C.): 233-235° C.
LC-MS: M+H=298
$^1$H NMR (DMSO) δ (ppm): 9.15 (broad s, 2H); 7.65 (t, 2H); 7.60 (d, 2H); 7.25 (t, 2H); 6.95 (d, 2H); 4.80 (qt, 1H); 3.25 (s, 2H); 3.15 (m, 2H); 2.65 (t, 2H); 2.15 (t, 2H); 2.00 (t, 2H).

9.4 3-methylcarbamoyl-isoxazol-5-ylmethyl 2-(4'-fluorobiphenyl-4-yloxy)-6-aza-spiro[3.4]octane-6-carboxylate

9.4a 3-methylcarbamoyl-isoxazol-5-ylmethyl 2-(4'-fluorobiphenyl-4-yloxy)-6-aza-spiro[3.4]octane-6-carboxylate (obtained from isomer 2a) (compound No. 32) (isomer I)

In a reaction tube, a mixture of 0.690 g (2.07 mmoles) of 2-(4'-fluorobiphenyl-4-yloxy)-6-aza-spiro[3.4]octane hydrochloride, obtained in stage 9.3a, 0.730 g (2.27 mmoles) of 3-methylcarbamoyl-isoxazol-5-ylmethyl 4-nitrophenyl carbonate, obtained in stage 6.1, 1.08 ml (6.20 mmoles) of N,N-diisopropylethylamine and 0.126 g (1.03 mmoles) of N,N-dimethylaminopyridine is dissolved in 10 ml of 1,2-dichloroethane. With the tube sealed, the medium is heated to 70° C. for 14 hrs with stirring. After return to ambient temperature, the medium is diluted with a 1N aqueous solution of caustic soda and extracted twice with dichloromethane. The combined organic phases are then successively washed twice with a 1N aqueous solution of caustic soda, once with a saturated aqueous solution of ammonium chloride and once with a saturated aqueous solution of sodium chloride. After drying over sodium sulphate, filtration and evaporation under reduced pressure, the residue is purified by silica gel chromatography eluting with a 98/2/0.2 mixture of dichloromethane, methanol and 30% aqueous ammonia. 0.875 g of the expected product is obtained in the form of a white powder.

Melting point (° C.): 149-151° C.
LC-MS: M+H=480
$^1$H NMR (DMSO) δ (ppm): 8.70 (s, 1H); 7.65 (t, 2H); 7.55 (d, 2H); 7.25 (t, 2H); 6.95 (d, 2H); 6.80 (s, 1H); 5.25 (s, 2H); 4.80 (qt, 1H); 3.35 (m, 4H); 2.80 (s, 3H); 2.50 (t, 2H); 2.15 (t, 2H); 1.95 (m, 2H).

9.4b 3-methylcarbamoyl-isoxazol-5-ylmethyl 2-(4'-fluorobiphenyl-4-yloxy)-6-aza-spiro[3.4]octane-6-carboxylate (obtained from isomer 2b) (compound No. 33) (isomer II)

The procedure described in Example 9, stage 9.4a is followed. From 0.53 g (1.59 mmoles) of 2-(4'-fluorobiphenyl-4-yloxy)-6-aza-spiro[3.4]-octane hydrochloride, obtained in stage 9.3b, 0.561 g (1.75 mmoles) of 3-methylcarbamoyl-isoxazol-5-ylmethyl 4-nitrophenyl carbonate, obtained in stage 6.1, 0.83 ml (4.76 mmoles) of N,N-diisopropylethylamine and 0.097 g (1.03 mmoles) of N,N-dimethylaminopyridine, and after purification by silica gel chromatography eluting with a 98/2/0.2 mixture of dichloromethane, methanol and aqueous ammonia, 0.638 g of the expected product are obtained in the form of a white powder.

Melting point (° C.): 150-152° C.
LC-MS: M+H=480
$^1$H NMR (DMSO) δ (ppm) 8.70 (broad s, 1H); 7.65 (t, 2H); 7.55 (d, 2H); 7.25 (t, 2H); 6.95 (d, 2H); 6.80 (d, 1H); 5.25 (s, 2H); 4.85 (qt, 1H); 3.45 (m, 2H); 3.35 (m, 2H); 2.80 (s, 3H); 2.50 (m, 2H); 2.10 (t, 2H); 1.95 (m, 2H).

EXAMPLE 10

Compound No. 24

3-carbamoyl-isoxazol-5-ylmethyl 6-(4-chloro-3-fluorophenoxy)-2-aza-spiro[3.3]heptane-2-carboxylate

10.1 Tert-butyl 5,5-dichloro-6-oxo-2-aza-spiro[3.3]-heptane-2-carboxylate

Under an inert atmosphere, 7.728 g (118.19 mmoles) of zinc in nanopowder form are suspended in 100 ml of diethyl ether. 5.00 g (29.55 mmoles) of tert-butyl 3-methylene-azetidine-1-carboxylate (WO 2008124085) are added, then the medium is cooled to 10° C. A solution of 6.60 ml (59.09 mmoles) of trichloroacetyl chloride in ml of 1,2-dimethoxyethane is added drop by drop while maintaining the temperature of the reaction medium between 26 and 30° C. After stirring for 14 hrs at ambient temperature, the medium is filtered over celite, the celite is copiously rinsed with diethyl ether and the filtrate is partially concentrated under reduced pressure. The crude reaction product thus obtained is used as such in the following stage.

10.2 Tert-butyl 6-oxo-2-aza-spiro[3.3]heptane-2-carboxylate 9.66 g (147.73 mmoles) of Zn powder are suspended in 150 ml of glacial acetic acid. The medium is cooled to 0° C. and the crude solution of tert-butyl 5,5-dichloro-6-oxo-2-azaspiro[3.3]-heptane-2-carboxylate, obtained in stage 10.1, in 30 ml of dioxan is added drop by drop. After stirring for 16 hrs at ambient temperature, the medium is slowly poured in portions into a saturated aqueous solution of sodium carbonate. After rebasification with sodium carbonate, the medium is stirred for one hour, then filtered on a fritted filter and the filtrate is extracted three times with ethyl acetate. The combined organic phases are washed once with a saturated aqueous solution of sodium chloride, dried over sodium sulphate, filtered and concentrated under vacuum. The residue is purified by silica gel chromatography eluting with a 90/10 then 80/20 and 60/40 mixture of cyclohexane and ethyl acetate. 2.4 g of the expected product are obtained in the form of a brown gum.

$^1$H NMR (DMSO) δ (ppm): 4.05 (s, 4H); 3.30 (s, 4H); 1.40 (s, 9H).

10.3 Tert-butyl 6-hydroxy-2-aza-spiro[3.3]heptane-2-carboxylate 0.494 g (13.06 mmoles) of sodium borohydride is added in portions at 0° C. to a solution of 2.30 g (10.89 mmoles) of tert-butyl 6-oxo-2-aza-spiro[3.3]-heptane-2-carboxylate, obtained in stage 10.2, in 55 ml of methanol. The reaction mixture is stirred for 1 hr at ambient temperature. After evaporation of the solvent, water is added to the reaction mixture, the aqueous phase is separated, it is extracted several times with dichloromethane, and the combined organic phases are washed with a saturated aqueous solution of sodium chloride, dried over sodium sulphate and the filtrate is concentrated under reduced pressure. After crystallisation of the residue in diisopropyl ether, filtration of the solid obtained and drying under vacuum at 60° C., 2.24 g of product are obtained in the form of a beige powder.

$^1$H NMR (DMSO) δ (ppm): 5.00 (d, 1H); 3.95 (hex, 1H); 3.75 (d, 4H); 2.40 (m, 2H); 1.95 (m, 2H); 1.40 (s, 9H).

10.4 Tert-butyl 6-(4-chloro-3-fluorophenoxy)-2-aza-spiro[3.3]-heptane-2-carboxylate The procedure described in Example 2, stage 2.1, is followed. From 1.50 g (7.03 mmoles) of tert-butyl 6-hydroxy-2-aza-spiro[3.3]heptane-2-carboxylate, obtained in stage 10.3, 1.237 g (8.44 mmoles) of 4-chloro-3-fluorophenol, 1.409 g (8.09 mmoles) of diethyl azo-dicarboxylate and 2.121 g (8.09 mmoles) of triphenylphosphine and after silica gel chromatography eluting with a 95/5, then 90/10 mixture of cyclohexane and ethyl acetate, 1.73 g of the expected product are obtained in the form of a beige powder.

Melting point (° C.): 110-112° C.
LC-MS: M+H=342
$^1$H NMR (DMSO) δ (ppm): 7.45 (t, 1H); 6.95 (d, 1H); 6.75 (d, 1H); 4.65 (qt, 1H); 3.90 (broad d, 4H); 2.75 (m, 2H); 2.20 (m, 2H); 1.40 (s, 9H).

10.5 6-(4-chloro-3-fluorophenoxy)-2-aza-spiro[3.3]-heptane trifluoroacetate 1.70 g (4.97 mmoles) of tert-butyl 6-(4-chloro-3-fluorophenoxy)-2-aza-spiro[3.3]heptane-2-carboxylate, obtained in stage 10.4, are dissolved in 40 ml of dichloromethane. The medium is cooled in an ice bath, then 8 ml (105.24 mmoles) of trifluoroacetic acid are added slowly. After stirring for 2 hrs at ambient temperature, the medium is diluted with 100 ml of toluene and concentrated under reduced pressure. The residue obtained is crystallised in diethyl ether to give a powder which is filtered off, rinsed with diethyl ether and dried under vacuum. 1.675 g of the expected product are obtained in the form of a hygroscopic pink powder.

LC-MS: M+H=242
$^1$H NMR (DMSO) δ (ppm): 8.75 (broad s, 2H); 7.45 (t, 1H); 6.95 (d, 1H); 6.75 (d, 1H); 4.65 (qt, 1H); 4.00 (broad d, 4H); 2.80 (m, 2H); 2.25 (m, 2H).

10.6 3-carbamoyl-isoxazol-5-ylmethyl 6-(4-chloro-3-fluorophenoxy)-2-aza-spiro[3.3]heptane-2-carboxylate The procedure described in example 7, stage 7.5, is followed. From 0.600 g (1.69 mmoles) of 6-(4-chloro-3-fluorophenoxy)-2-aza-spiro[3.3]heptane trifluoroacetate obtained in stage 10.5, 0.622 g (2.02 mmoles) of 3-carbamoylisoxazol-5-ylmethyl 4-nitrophenyl carbonate, obtained in stage 7.4, 1.03 ml (5.90 mmoles) of N,N-diisopropylethylamine and 0.021 g (0.17 mmole) of N,N-dimethylaminopyridine, and after silica gel chromatography eluting with a 99/1/0.1 then 98/2/0.2 mixture of dichloromethane, methanol and 30% aqueous ammonia. 0.602 g of the expected product are obtained in the form of a white powder.

Melting point (° C.): 135-137° C.
LC-MS: M+H=410
$^1$H NMR (DMSO) δ (ppm): 8.15 (s, 1H); 7.85 (s, 1H); 7.45 (t, 1H); 6.95 (d, 1H); 6.80 (s, 1H); 6.75 (d, 1H); 5.20 (s, 2H); 4.65 (qt, 1H); 4.10-3.90 (broad d, 4H); 2.75 (m, 2H); 2.25 (m, 2H).

EXAMPLE 11

Compound No. 25

3-methylcarbamoyl-isoxazol-5-ylmethyl 6-(4'fluoro-biphenyl-4-yloxy)-2-aza-spiro[3.3]heptane-2-carboxylate

11.1 Tert-butyl 6-(4'fluorobiphenyl-4-yloxy)-2-aza-spiro[3.3]heptane-2-carboxylate The procedure described in Example 2, stage 2.1, is followed. From 0.900 g (4.22 moles) of tert-butyl 6-hydroxy-2-aza-spiro[3.3]heptane-2-carboxylate, obtained in stage 10.3, 0.953 g (5.06 mmoles) of 4'-fluorobiphenyl-4-ol, 0.845 g (4.85 mmoles) of diethyl azo-dicarboxylate and 1.328 g (5.06 mmoles) of triphenylphosphine, and after silica gel chromatography eluting with a 95/5, then 90/10 mixture of cyclohexane and ethyl acetate, 1.44 g of the expected product are obtained in the form of a beige powder used as such in the following stage.

11.2 6-(4'fluorobiphenyl-4-yloxy)-2-aza-spiro[3.3]-heptane trifluoroacetate

The procedure described in Example 10, stage 10.5, is followed. From 1.44 g (3.76 mmoles) of tert-butyl 6-(4'fluorobiphenyl-4-yloxy)-2-aza-spiro[3.3]heptane-2-carboxylate, obtained in stage 11.1, and 8 ml (105.24 mmoles) of trifluoroacetic acid, 1.04 g of the expected product are obtained in the form of a hygroscopic powder.

LC-MS: M+H=284
$^1$H NMR (DMSO) δ (ppm): 8.60 (broad s, 1H); 7.65 (t, 2H); 7.60 (d, 2H); 7.25 (t, 2H); 6.90 (d, 2H); 4.70 (qt, 1H); 4.05 (broad d, 4H); 2.85 (m, 2H); 2.30 (m, 2H).

11.3 3-methylcarbamoyl-isoxazol-5-ylmethyl 6-(4'fluorobiphenyl-4-yloxy)-2-aza-spiro[3.3]-heptane-2-carboxylate The procedure described in Example 7, stage 7.5, is followed. From 0.500 g (1.26 mmoles) of 6-(4'fluorobiphenyl-4-yloxy)-2-aza-spiro[3.3]heptane trifluoroacetate, obtained in stage 11.2, 0.485 g (1.51 mmoles) of 3-methylcarbamoyl-isoxazol-5-ylmethyl 4-nitrophenyl carbonate, obtained in stage 6.1, 0.77 ml (4.40 mmoles) of N,N-diisopropylethylamine and 0.015 g (0.13 mmole) of N,N-dimethylaminopyridine, and after silica gel chromatography eluting with a 99/1/0.1 mixture of dichloromethane, methanol and 30% aqueous ammonia. 0.538 g of the expected product is obtained in the form of a white powder.

Melting point (° C.): 163-165° C.

LC-MS: M+H=466

$^1$H NMR (DMSO) δ (ppm): 8.70 (qd, 1H); 7.65 (t, 2H); 7.55 (d, 2H); 7.25 (t, 2H); 6.90 (d, 2H); 6.80 (s, 1H); 5.20 (s, 2H); 4.65 (qt, 1H); 4.10-3.90 (broad d, 4H); 2.80 (d, 3H); 2.75 (m, 2H); 2.25 (m, 2H).

Table 1 below illustrates the chemical structures and the physical properties of some compounds according to the invention. In this table, the compounds are in free base or salt form.

TABLE 1

(I)

| N° | R$_1$ | m | n | o | p | A | R$_2$ | R$_3$ | R$_4$ | Base or salt |
|---|---|---|---|---|---|---|---|---|---|---|
| 1. | 4-Cl-phenyl | 2 | 2 | 1 | 1 | O | H | H | thiazolyl | base |
| 2. | 4-Cl-phenyl | 2 | 2 | 1 | 1 | O | H | H | 1-methyl-1,2,4-triazolyl | HCl |
| 3. | 4-Cl-phenyl | 2 | 2 | 1 | 1 | O | H | H | isoxazol-3-carboxamide-N-methyl | base |
| 4. | 4-Cl-phenyl | 2 | 2 | 1 | 1 | O | H | H | isoxazol-3-carboxamide | base |
| 5. | 3-CF$_3$-phenyl | 2 | 2 | 1 | 1 | O | H | H | isoxazol-3-carboxamide-N-methyl | base |
| 6. | 3-CF$_3$-phenyl | 2 | 2 | 1 | 1 | O | H | H | isoxazol-3-carboxamide | base |
| 7. | 4'-F-biphenyl-3-yl | 2 | 2 | 1 | 1 | O | H | H | isoxazol-3-carboxamide-N-methyl | base |

TABLE 1-continued (I)

| N° | R₁ | m | n | o | p | A | R₂ | R₃ | R₄ | Base or salt |
|---|---|---|---|---|---|---|---|---|---|---|
| 8. | 7-ethoxy-naphthalen-2-yl | 2 | 2 | 1 | 1 | O | H | H | 5-(N-methylcarbamoyl)isoxazol-3-yl | base |
| 9. | 3-(trifluoromethyl)phenyl | 2 | 1 | 1 | 1 | O | H | H | 5-carbamoyl-isoxazol-3-yl | HCl |
| 10. | 3-(trifluoromethyl)phenyl | 2 | 1 | 1 | 1 | O | H | H | 5-carbamoyl-isoxazol-3-yl (Isomer I) | base |
| 11. | 3-(trifluoromethyl)phenyl | 2 | 1 | 1 | 1 | O | H | H | 5-carbamoyl-isoxazol-3-yl (Isomer II) | base |
| 12. | 4'-fluoro-biphenyl-3-yl | 2 | 2 | 1 | 1 | O | H | H | 5-carbamoyl-isoxazol-3-yl | base |
| 13. | 7-ethoxy-naphthalen-2-yl | 2 | 2 | 1 | 1 | O | H | H | 5-carbamoyl-isoxazol-3-yl | base |
| 14. | 3-(trifluoromethyl)phenyl | 2 | 1 | 1 | 1 | O | H | H | 4-carbamoyl-oxazol-2-yl | base |
| 15. | 3-(trifluoromethyl)phenyl | 2 | 1 | 1 | 1 | O | H | H | 4-(N-methylcarbamoyl)oxazol-2-yl | base |

TABLE 1-continued
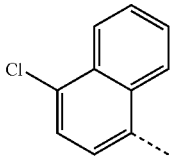
(I)
| N° | R₁ | m | n | o | p | A | R₂ | R₃ | R₄ | Base or salt |
|---|---|---|---|---|---|---|---|---|---|---|
| 16. | 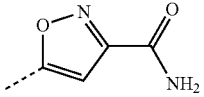 | 2 | 2 | 1 | 1 | O | H | H | 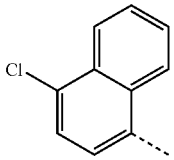 | base |
| 17. | 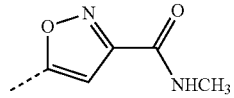 | 2 | 2 | 1 | 1 | O | H | H | 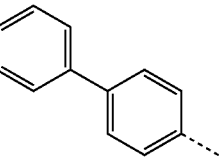 | base |
| 18. | 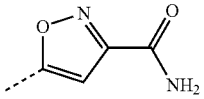 | 2 | 2 | 1 | 1 | O | H | H | 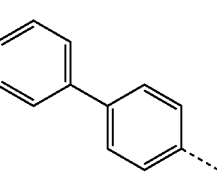 | base |
| 19. | 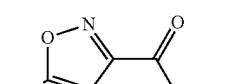 | 2 | 2 | 1 | 1 | O | H | H | 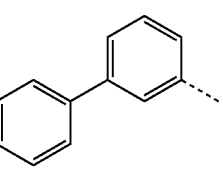 | base |
| 20. | 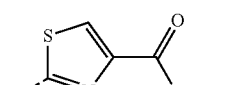 | 2 | 2 | 1 | 1 | O | H | H | 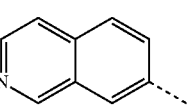 | base |
| 21. | 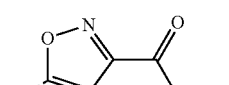 | 2 | 2 | 1 | 1 | O | H | H | 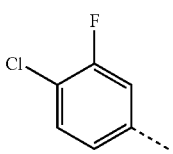 | base |
| 22. | 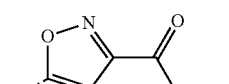 | 2 | 2 | 1 | 1 | O | H | H | 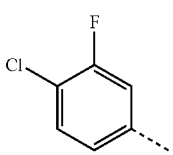 | base |
| 23. | 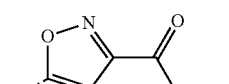 | 1 | 1 | 1 | 1 | O | H | H | 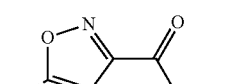 | base |

TABLE 1-continued
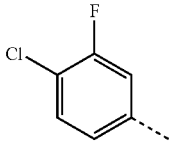
(I)
| N° | R₁ | m | n | o | p | A | R₂ | R₃ | R₄ | Base or salt |
|---|---|---|---|---|---|---|---|---|---|---|
| 24. | 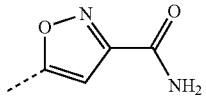 | 1 | 1 | 1 | 1 | O | H | H | 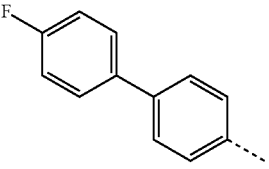 | base |
| 25. | 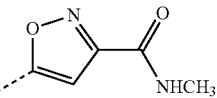 | 1 | 1 | 1 | 1 | O | H | H | 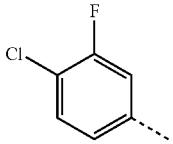 | base |
| 26. | 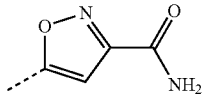 | 2 | 1 | 1 | 1 | O | H | H | 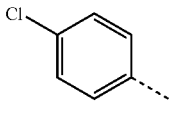 | base |
| 27. | 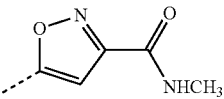 | 2 | 1 | 1 | 1 | O | H | H | 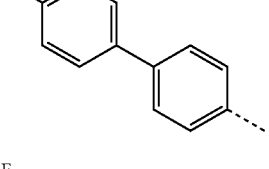 | base |
| 28. | 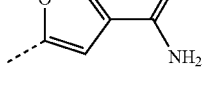 | 2 | 1 | 1 | 1 | O | H | H | 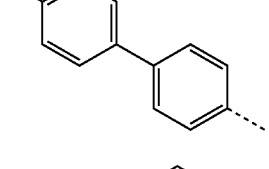 | base |
| 29. | 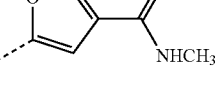 | 2 | 1 | 1 | 1 | O | H | H | 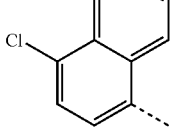 | base |
| 30. | 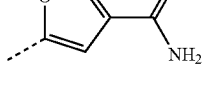 | 2 | 1 | 1 | 1 | O | H | H | 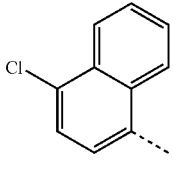 | base |
| 31. | 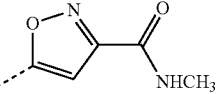 | 2 | 1 | 1 | 1 | O | H | H |  | base |

TABLE 1-continued (I)

| N° | R₁ | m | n | o | p | A | R₂ | R₃ | R₄ | Base or salt |
|---|---|---|---|---|---|---|---|---|---|---|
| 32. | 4'-fluorobiphenyl | 2 | 1 | 1 | 1 | O | H | H | isoxazole-C(O)NHCH₃ (Isomer I) | base |
| 33. | 4'-fluorobiphenyl | 2 | 1 | 1 | 1 | O | H | H | isoxazole-C(O)NHCH₃ (Isomer II) | base |

Table 2 below gives the results of ¹H NMR analyses, melting points (MP) and M+H masses measured for the compounds in Table 1.

TABLE 2

| N° | 1H NMR, 400 Mhz DMSO/CDCl₃ | MP | M + H |
|---|---|---|---|
| 1 | δ (ppm) CDCl₃: 8.85 (s, 1H); 7.40 (s, 1H); 7.30 (t, 2H); 6.80 (d, 2H); 5.35 (s, 2H); 4.70 (qt, 1H); 3.35 (m, 4H); 2.45 (m, 2H); 2.00 (m, 2H); 1.65 (m, 4H). | 86-88° C. | 393 |
| 2 | 7.8 (d, 1H); 7.75 (d, 1H); 7.35 (d, 2H); 6.90 (d, 2H); 5.35 (s, 2H); 4.95 (m, 2H); 3.55 (m, 2H); 3.25 (broad m, 2H); 2.85 (broad m, 2H); 2.0 (m, 2H); 1.85 (m, 2H). | 163-165° C | 391 |
| 3 | δ (ppm) DMSO: 8.85 (s, 1H); 7.35 (d, 2H); 6.90 (d, 2H); 6.80 (s, 1H); 5.25 (s, 2H); 4.75 (qt, 1H); 3.35 (broad d, 4H); 2.80 (s, 3H); 2.45 (m, 2H); 1.80 (m, 2H); 1.55 (dt, 4H). | 147-149° C. | 434 |
| 4 | δ (ppm) DMSO: 8.15 (s, 1H); 7.85 (s, 1H); 7.30 (d, 2H); 6.90 (d, 2H); 6.80 (s, 1H); 5.25 (s, 2H); 4.75 (qt, 1H); 3.35 (broad d, 4H); 2.45 (t, 2H); 1.80 (t, 2H); 1.55 (d, 4H). | 70-72° C. | 420 |
| 5 | δ (ppm) DMSO: 8.70 (s, 1H); 7.45 (t, 1H); 7.30 (d, 1H); 7.15 (d, 1H); 7.10 (s, 1H); 6.80 (s, 1H); 5.25 (s, 2H); 4.85 (m, 1H); 3.35 (broad d, 4H); 2.80 (s, 3H); 2.45 (m, 2H); 1.85 (m, 2H); 1.55 (d, 4H). | 93-95° C. | 468 |
| 6 | δ (ppm) DMSO: 8.10 (s, 1H); 7.85 (s, 1H); 7.50 (t, 1H); 7.25 (d, 1H); 7.15 (d, 1H); 7.10 (s, 1H); 6.80 (s, 1H); 5.25 (s, 2H); 4.85 (qt, 1H); 3.35 (broad d, 4H); 2.45 (m, 2H); 1.85 (m, 2H); 1.55 (d, 4H). | 88-90° C. | 454 |
| 7 | δ (ppm) DMSO: 8.70 (s, 1H); 7.70 (t, 2H); 7.40 (t, 1H); 7.30 (t, 2H); 7.20 (d, 1H); 7.10 (s, 1H); 6.85 (d, 1H); 6.80 (s, 1H); 5.25 (s, 2H); 4.85 (qt, 1H); 3.35 (broad d, 4H); 2.80 (s, 3H); 2.50 (m, 2H); 1.85 (m, 2H); 1.55 (d, 4H). | 94-96° C. | 494 |
| 8 | δ (ppm) DMSO: 8.70 (broad s, 1H); 7.70 (d, 2H); 7.20 (s, 1H); 7.10 (s, 1H); 6.95 (t, 2H); 6.80 (s, 1H); 5.25 (s, 2H); 4.85 (qt, | 73-75° C. | 494 |

TABLE 2-continued

| N° | 1H NMR, 400 Mhz DMSO/CDCl₃ | MP | M + H |
|---|---|---|---|
|  | 1H); 4.15 (qd, 2H); 3.40 (broad d, 4H); 2.80 (s, 3H); 2.55 (m, 2H); 1.90 (m, 2H); 1.60 (dt, 4H); 1.40 (t, 3H). |  |  |
| 9 | δ (ppm) DMSO: 8.15 (s, 1H); 7.80 (s, 1H); 7.50 (t, 1H); 7.30 (d, 1H); 7.15 (m, 2H); 6.80 (d, 1H); 5.25 (d, 2H); 4.90 (m, 1H); 3.45 (s, 2H); 3.35 (m, 2H); 2.55 (m, 2H); 2.10 (m, 2H); 1.95 (m, 2H). | oil | 440 |
| 10 | δ (ppm) DMSO: 8.15 (s, 1H); 7.85 (s, 1H); 7.55 (t, 1H); 7.30 (d, 1H); 7.20 (d, 1H), 7.15 (s, 1H); 6.85 (d, 1H); 5.25 (s, 2H); 4.90 (qt, 1H); 3.45 (s, 2H); 3.30 (m, 2H); 2.55 (m, 2H); 2.05 (m, 2H); 1.95 (m, 2H). | 97-99° C. | 440 |
| 11 | δ (ppm) DMSO: 8.10 (s, 1H); 7.85 (s, 1H); 7.55 (t, 1H); 7.30 (d, 1H); 7.20 (d, 1H), 7.15 (s, 1H); 6.80 (s, 1H); 5.25 (s, 2H); 4.85 (qt, 1H); 3.45-3.25 (m, 4H); 2.50 (m, 2H); 2.10 (m, 2H); 1.95 (m, 2H). | wax | 440 |
| 12 | δ (ppm) DMSO: 8.10 (s, 1H); 7.85 (s, 1H); 7.55 (t, 1H); 7.30 (d, 1H); 7.20 (d, 1H), 7.15 (s, 1H); 6.80 (s, 1H); 5.25 (s, 2H); 4.85 (qt, 1H); 3.45-3.25 (m, 4H); 2.50 (m, 2H); 2.10 (m, 2H); 1.95 (m, 2H). | 74-76° C. | 480 |
| 13 | δ (ppm) DMSO: 8.10 (s, 1H); 7.85 (s, 1H); 7.55 (t, 1H); 7.30 (d, 1H); 7.20 (d, 1H), 7.15 (s, 1H); 6.80 (s, 1H); 5.25 (s, 2H); 4.85 (qt, 1H); 3.45-3.25 (m, 4H); 2.50 (m, 2H); 2.10 (m, 2H); 1.95 (m, 2H). | 114-116° C. | 480 |
| 14 | δ (ppm) DMSO: 8.60 (d, 1H); 7.65 (broad s, 1H); 7.50 (m, 2H); 7.30 (d, 1H); 7.15 (m, 2H); 5.20 (d, 2H); 4.90 (m, 1H); 3.45 (s, 2H); 3.35 (m, 2H); 2.55 (m, 2H); 2.10 (m, 2H); 1.95 (m, 2H). | 90-92° C. | 440 |
| 15 | δ (ppm) DMSO: 8.60 (d, 1H); 8.25 (broad s, 1H); 7.55 (t, 1H); 7.30 (d, 2H); 7.15 (m, 2H); 5.20 (d, 2H); 4.90 (m, 1H); 3.45 (s, 2H); 3.35 (m, 2H); 2.75 (s, 3H); 2.55 (m, 2H); 2.10 (m, 2H); 1.95 (m, 2H). | wax | 454 |
| 16 | δ (ppm) DMSO: 8.25 (d, 1H); 8.15 (d, 2H); 7.85 (s, 1H); 7.75 (t, 1H); 7.65 (t, 1H), 7.60 (d, 1H); 6.80 (d, 2H); 5.25 (s, 2H); 4.95 (qt, 1H); 3.40 (broad d, 4H); 2.55 (m, 2H); 1.95 (m, 2H); 1.60 (dt, 4H). | 75-77° C. | 468 |
| 17 | δ (ppm) DMSO: 8.70 (s, 1H); 8.25 (d, 1H); 8.15 (d, 1H); 7.75 (t, 1H); 7.65 (t, 1H), 7.60 (d, 1H); 6.80 (d, 2H); 5.25 (s, 2H); 4.95 (qt, 1H); 3.40 (broad d, 4H); 2.80 (s, 3H); 2.55 (m, 2H); 1.95 (m, 2H); 1.60 (dt, 4H). | 62-64° C. | 484 |
| 18 | δ (ppm) DMSO: 8.15 (s, 1H); 7.85 (s, 1H); 7.65 (t, 2H); 7.55 (d, 2H); 7.25 (t, 2H), 6.95 (d, 2H); 6.80 (s, 1H); 5.25 (s, 2H); 4.80 (qt, 1H); 3.35 (broad d, 4H); 2.45 (m, 2H); 1.85 (m, 2H); 1.60 (dt, 4H). | 163-165° C. | 497* |
| 19 | δ (ppm) DMSO: 8.70 (s, 1H); 7.65 (t, 2H); 7.55 (d, 2H); 7.25 (t, 2H); 6.95 (d, 2H); 6.80 (s, 1H); 5.25 (s, 2H); 4.80 (qt, 1H); 3.35 (broad d, 4H); 2.80 (s, 3H); 2.45 (m, 2H); 1.85 (m, 2H); 1.60 (dt, 4H). | 174-176° C. | 494 |
| 20 | δ (ppm) DMSO: 8.35 (broad s, 1H); 8.25 (s, 1H); 7.70 (t, 2H); 7.35 (t, 1H); 7.30 (t, 2H); 7.20 (d, 1H); 7.05 (s, 1H); 6.85 (d, 1H); 5.35 (s, 2H); 4.90 (qt, 1H); 3.40 (broad d, 4H); 2.80 (s, 3H); 2.50 (m, 2H); 1.85 (m, 2H); 1.60 (dt, 4H). | 130-132° C. | 510 |
| 21 | δ (ppm) DMSO: 9.20 (s, 1H); 8.70 (broad s, 1H); 8.40 (d, 1H); 7.90 (d, 1H); 7.75 (d, 1H); 7.40 (t, 2H); 6.80 (s, 1H); 5.25 (s, 2H); 4.95 (qt, 1H); 3.40 ( broad d, 4H); 2.80 (s, 3H); 2.60 (m, 2H); 1.90 (m, 2H); 1.60 (dt, 4H). | 79-81° C. | 451 |
| 22 | δ (ppm) DMSO: 8.70 (broad s, 1H); 7.45 (t, 1H); 6.95 (d, 1H); 6.80 (s, 1H); 6.75 (d, 1H); 5.25 (s, 2H); 4.80 (qt, 1H); 3.35 (broad d, 4H); 2.80 (s, 3H); 2.45 (m, 2H); 1.85 (m, 2H); 1.55 (dt, 4H). | 107-108° C. | 452 |

TABLE 2-continued

| N° | 1H NMR, 400 Mhz DMSO/CDCl₃ | MP | M + H |
|---|---|---|---|
| 23 | δ (ppm) DMSO: 8.70 (qd, 1H); 7.45 (t, 1H); 6.90 (d, 1H); 6.80 (s, 1H); 6.75 (d, 1H); 5.20 (s, 2H); 4.65 (qt, 1H); 4.10-3.90 (broad d, 4H); 2.80 (d, 3H); 2.75 (m, 2H); 2.25 (m, 2H). | 84-86° C. | 424 |
| 24 | δ (ppm) DMSO: 8.15 (s, 1H); 7.85 (s, 1H); 7.45 (t, 1H); 6.95 (d, 1H); 6.80 (s, 1H); 6.75 (d, 1H); 5.20 (s, 2H); 4.65 (qt, 1H); 4.10-3.90 (broad d, 4H); 2.75 (m, 2H); 2.25 (m, 2H). | 135-137° C. | 410 |
| 25 | δ (ppm) DMSO: 8.70 (qd, 1H); 7.65 (t, 2H); 7.55 (d, 2H); 7.25 (t, 2H); 6.90 (d, 2H); 6.80 (s, 1H); 5.20 (s, 2H); 4.65 (qt, 1H); 4.10-3.90 (broad d, 4H); 2.80 (d, 3H); 2.75 (m, 2H); 2.25 (m, 2H). | 163-165° C. | 466 |
| 26 | δ (ppm) DMSO: 8.15 (s, 1H); 7.85 (s, 1H); 7.45 (t, 1H); 7.00 (d, 1H); 6.80 (m, 2H); 5.25 (d, 2H); 4.80 (m, 1H); 3.35 (m, 4H); 2.55 (m, 2H); 2.10 (m, 2H); 1.95 (m, 2H). | 83-92° C. | 424 |
| 27 | δ (ppm) DMSO: 8.70 (broad s, 1H); 7.30 (d, 2H); 6.90 (d, 2H); 6.80 (d 1H); 5.25 (d, 2H); 4.75 (m, 1H); 3.35 (m, 4H); 2.80 (s, 3H); 2.50 (m, 2H); 2.05 (m, 2H); 1.95 (m, 2H). | 94-97° C. | 420 |
| 28 | δ (ppm) DMSO: 8.15 (s, 1H); 7.85 (s, 1H) 7.65 (t, 2H); 7.55 (d, 2H); 7.25 (t, 2H); 6.95 (d, 2H); 6.80 (d, 1H); 5.25 (d, 2H); 4.85 (m, 1H); 3.45 (d, 2H); 3.35 (m, 2H); 2.55 (m, 2H); 2.10 (m, 2H); 1.95 (m, 2H). | 131-133° C. | 466 |
| 29 | δ (ppm) DMSO: 8.70 (broad s, 1H); 7.65 (t, 2H); 7.55 (d, 2H); 7.25 (t, 2H); 6.95 (d, 2H); 6.80 (d, 1H); 5.25 (d, 2H); 4.80 (m, 1H); 3.35 (m, 4H); 2.80 (s, 3H); 2.50 (m, 2H); 2.10 (m, 2H), 1.95 (m, 2H). | 135-137° C. | 480 |
| 30 | δ (ppm) DMSO: 8.25 (d, 1H); 8.15 (d, 2H); 7.85 (broad s, 1H); 7.75 (t, 1H); 7.65 (t, 1H); 7.55 (d, 1H); 6.85 (d, 1H); 6.80 (s, 1H); 5.25 (d, 2H); 5.00 (m, 1H); 3.40 (m, 4H); 2.65 (m, 2H); 2.20 (m, 2H); 2.00 (m, 2H). | 149-150° C. | 456 |
| 31 | δ (ppm) DMSO: 8.70 (s, 1H); 8.25 (d, 1H); 8.15 (d, 1H); 7.75 (t, 1H); 7.65 (t, 1H); 7.55 (d, 1H); 6.85 (d, 1H); 6.80 (s, 1H); 5.25 (d, 2H); 5.00 (m, 1H); 3.40 (m, 4H); 2.80 (s, 3H); 2.60 (m, 2H); 2.20 (m, 2H); 2.00 (m, 2H). | 87-92° C. | 470 |
| 32 | δ (ppm) DMSO: 8.70 (s, 1H); 7.65 (t, 2H); 7.55 (d, 2H); 7.25 (t, 2H); 6.95 (d, 2H); 6.80 (s, 1H); 5.25 (s, 2H); 4.80 (qt, 1H); 3.35 (m, 4H); 2.80 (s, 3H); 2.50 (t, 2H); 2.15 (t, 2H); 1.95 (m, 2H). | 149-151° C. | 480 |
| 33 | δ (ppm) DMSO: 8.70 (broad s, 1H); 7.65 (t, 2H); 7.55 (d, 2H); 7.25 (t, 2H); 6.95 (d, 2H); 6.80 (d, 1H); 5.25 (s, 2H); 4.85 (qt, 1H); 3.45 (m, 2H); 3.35 (m, 2H); 2.80 (s, 3H); 2.50 (m, 2H); 2.10 (t, 2H); 1.95 (m, 2H). | 150-152° C. | 480 |

*M + NH4+ peak observed

Table 3 below shows the relative proportions and retention times of the isomers of the compounds 9, 14, 15, 26, 27, 28, 29, 30 and 31, obtained from one of the two chromatographic analysis methods below:

Method 1:
HPLC/ZQ→Gradient 10 min
Mobile phases: Phase A: CH3COONH4+3% ACN
Phase B: ACN
Stationary phase/column: Kromasil C18 column,
Dimensions: 50×2.1 mm; 3.5 μm
Flow rate: D=0.8 ml/min
Column temperature: T=40° C.
Injection volume: V=5 μl
Gradient: T=0 min: 100% A; from T=5.5 mins to T=7 mins: 100% B; from T=7.1 mins to T=10 mins: 100% A Method 2:
UPLC/TOF—Gradient 3 min
Mobile phases: Phase A: H20+0.05% of TFA
Phase B: ACN+0.035% of TFA
Stationary phase/column: Acquity BEH C18 column,
Dimensions: 50×2.1 mm; 1.7 μm
Flow rate: D=1.0 ml/min
Column temperature: T=40° C.
Injection volume: V=2 μl
Gradient: T=0 min: 98% A and 2% B; from T=1.6 mins to T=2.1 mins: 100% B; from T=2.5 mins to T=3 mins: 98% A and 2% B.

TABLE 3

| N° | Method | MH+ | Isomer I (retention time/UV purity) | Isomer II (retention time/UV purity) |
|----|--------|-----|--------------------------------------|---------------------------------------|
| 9  | 1      | 440 | rt = 1.20 min/42.22%                 | rt = 1.22 min/51.52%                  |
| 14 | 2      | 440 | rt = 1.15 min/46.70%                 | rt = 1.17 min/52.00%                  |
| 15 | 2      | 454 | rt = 1.19 min/45.66%                 | rt = 1.22 min/51.46%                  |
| 26 | 2      | 424 | rt = 1.16 min/60.02%                 | rt = 1.19 min/36.63%                  |
| 27 | 2      | 420 | rt = 1.22 min/52.47%                 | rt = 1.24 min/47.53%                  |
| 28 | 2      | 466 | rt = 1.26 min/51.60%                 | rt = 1.28 min/47.34%                  |
| 29 | 2      | 480 | rt = 1.30 min/51.76%                 | rt = 1.32 min/47.13%                  |
| 30 | 1      | 456 | rt = 4.80 min/50.99%                 | rt = 4.90 min/46.53%                  |
| 31 | 1      | 470 | rt = 4.92 min/52.70%                 | rt = 5.02 min/45.90%                  |

The compounds of the invention were subjected to pharmacological tests to determine their inhibitory effect on the enzyme FAAH (Fatty Acid Amide Hydrolase).

Protocol 1

The inhibitory activity was demonstrated in a radio-enzymatic test based on measurement of the product of hydrolysis of [1-$^3$H ethanolamine] anandamide by FAAH (*Life Sciences* (1995), 56, 1999-2005 and *Journal of Biochemical and Biophysical Methods* (2004), 60(2), 171-177). Thus, mouse brains (minus the cerebellum) are removed and stored at −80° C. The membrane homogenates are prepared extemporaneously by homogenizing the tissues using a Precellys® machine in the reaction buffer (10 mM Tris-HCl, pH=8, 150 mM NaCl and 1 mM ethylenediaminetetraacetic acid (EDTA)). The enzymatic reaction is performed in 96-well Multiscreen filtration plates in a final volume of 70 µl. Reaction buffer supplemented with fatty acid-free bovine serum albumin (BSA, 1 mg/ml) is used for the enzymatic reaction and the dilution of the compounds and the [1-$^3$H ethanolamine] anandamide. The reaction buffer containing BSA (43 µl/well), the diluted test compounds at different concentrations (7 µl/well containing 1% DMSO) and the membrane preparation (10 µl/well, i.e. 200 µg of tissue per test) are successively added to the wells. After preincubation of the compounds with the enzyme at 25° C. for 20 mins, the reaction is started by adding [1-$^3$H ethanolamine] anandamide. (Specific activity 15-20 Ci/mmol) diluted with cold anandamide (10 µl/well, final concentration 10 µM, 0.01 µCi per test). After incubation for 20 mins at 25° C., the enzymatic reaction is stopped by addition of a 5M solution of active charcoal prepared in 1.5M NaCl and 0.5M HCl buffer (50 µl/well). The mixture is stirred for 10 mins and the aqueous phase containing the [1-$^3$H]ethanolamine is then recovered by filtration under vacuum and counted by liquid scintillation.

Protocol 2

The inhibitory activity was demonstrated by the fluorescence technique in an enzymatic test based on measurement of the fluorescent product of hydrolysis of arachidonyl 7-amino 4-methyl coumarin amide (AAMC) by FAAH (*Analytical Biochemistry* (2005), 343: 143-151, *J. of Biomolecular Screening* (2006), 11(5): 519-527 and *J. of Neurosciences Methods* (2007), 161: 47-54). Thus, mouse brains (minus the cerebellum) are removed and stored at −80° C. The brain homogenates are prepared extemporaneously by homogenizing the tissues using a Precellys® machine in the reaction buffer (10 mM Tris-HCl, pH=8, 150 mM NaCl and 1 mM ethylenediamine-tetraacetic acid (EDTA)). The enzymatic reaction is performed in black polystyrene 384-well plates in a final volume of 50 µl. Reaction buffer supplemented with fatty acid-free bovine serum albumin (BSA, 1 mg/ml) is used for the enzymatic reaction, dilution of the compounds and dilution of the AAMC. The reaction buffer containing BSA (25 µl/well), the diluted test compounds at different concentrations (5 µl/well containing 1% DMSO) and the membrane preparation (10 µl/well, i.e. 200 µg of tissue per test) are successively added to the wells. After preincubation of the compounds with the enzyme for 20 mins at 25° C., the reaction is started by addition of 10 µl of substrate per well (AAMC, final concentration 10 µM). After incubation for 40 mins at 37° C., the aminomethyl coumarin (AMC) produced is measured by fluorescent counting (Envision plate reader).

Under the conditions of protocol 1, the most active compounds of the invention have $IC_{50}$ (concentration inhibiting 50% of the control enzymatic activity of FAAH) values lying between 0.001 and 1 µM; for example, compounds 7, 29, 32 and 33 have respective $IC_{50}$ values of 19 nM 5.3 nM, 3 nM and 19 nM.

Under the conditions of protocol 2, the most active compounds of the invention have $IC_{50}$ (concentration inhibiting 50% of the control enzymatic activity of FAAH) values lying between 0.001 and 1 µM; for example, compounds 19 and 25 have respective $IC_{50}$ values of 1.7 nM and 0.46 nM.

It thus appears that the compounds according to the invention have inhibitory activity on the enzyme FAAH.

The in vivo activity of the compounds of the invention was evaluated in a test of analgesia.

Thus, the intraperitoneal (i.p.) administration of PBQ (phenylbenzoquinone, 2 mg/kg in 0.9% sodium chloride solution containing 5% ethanol) to male OF1 mice weighing 25 to 30 g causes abdominal stretching, on average 30 torsions or contractions during the period of 5 to 15 mins after injection. The test compounds are administered orally (p.o.) or intraperitoneally (i.p.) suspended in Tween 80 at 0.5%, 60 mins or 120 mins before the administration of PBQ. Under these conditions, the most powerful compounds reduce by 35% to 80% the number of stretches induced by the PBQ, in a dosage range lying between 1 and 30 mg/kg. For example, compound 25 of Table 1 reduces by 50% the number of stretches induced by the PBQ, at a dose of 30 mg/kg p.o. at 120 mins.

The enzyme FAAH (*Chemistry and Physics of Lipids*, (2000), 108, 107-121) catalyses the hydrolysis of the endogenous amide and ester derivatives of various fatty acids such as N-arachidonoylethanolamine (anandamide), N-palmitoylethanolamine, N-oleoylethanolamine, oleamide or 2-arachidonoylglycerol. These derivatives exert different pharmacological activities by interacting, inter alia, with the cannabinoid and vanilloid receptors.

The compounds of the invention block this degradation pathway and increase the tissue levels of these endogenous substances. Hence, they can be used in the prevention and treatment of pathologies in which the endogenous cannabinoids and/or any other substrates metabolized by the enzyme FAAH are involved. The following diseases and complaints can for example be cited:

pain, especially acute or chronic pain of neurogenic type: migraine, neuropathic pain including the forms associated with the herpes virus and diabetes and with chemotherapy, acute or chronic pain associated with inflammatory diseases: arthritis, rheumatoid arthritis, osteoarthritis, spondylitis, gout, vascularitis, Crohn's disease, irritable bowel syndrome, acute or chronic peripheral pain, vertigo, vomiting, nausea, in particular post-chemotherapy nausea, eating disorders, in particular anorexia and cachexia of diverse nature, neurological and psychiatric disorders: tremor, dyskinaesia, dystonia, spasticity, compulsive and obsessive behaviour, Tourette's syndrome, all forms of depression and anxiety of any nature or origin, mood disorders, psychoses, acute and chronic neuro-degenerative diseases: Parkinson's disease, Alzheimer's disease, senile dementia, Huntington's chorea, lesions associated with cerebral ischaemia and cranial and medullary trauma, epilepsy, sleep disorders, including sleep apnoea, cardiovascular diseases, in particular hypertension, cardiac arrhythmia, arteriosclerosis, heart attack, cardiac ischaemia, renal ischaemia, cancers: benign skin tumours, papillomas and cerebral tumours, prostate tumours, cerebral tumours (glioblastomas, medullo-epitheliomas, medullo-blastomas, neuroblastomas, tumours of embryonic origin, astrocytomas, astroblastomas, ependyomas, oligodendro-gliomas, plexus tumour, neuroepitheliomas, pineal gland tumours, ependymoblastomas, malignant meningiomas, sarcomatoses, malignant melanomas, schwannomas), immune system disorders, especially autoimmune diseases: psoriasis, lupus erythematosus, connective tissue diseases or connectivitis, Sjögrer's syndrome, ankylosing spondylitis, undifferentiated spondylitis, Behcet's disease, haemolytic autoimmune anaemias, multiple sclerosis, amyotrophic lateral sclerosis, amylosis, graft rejection, diseases affecting the plasmocytic line, allergic diseases: immediate or delayed hyper-sensitivity, allergic rhinitis or allergic conjunctivitis, contact dermatitis, parasitic, viral or bacterial infectious diseases: AIDS, meningitis, inflammatory diseases, especially articular diseases: arthritis, rheumatoid arthritis, osteoarthritis, spondylitis, gout, vascularitis, Crohn's disease, irritable bowel syndrome, osteoporosis, ocular complaints: ocular hypertension, glaucoma, pulmonary complaints: respiratory tract diseases, bronchospasm, cough, asthma, chronic bronchitis, chronic obstruction of the respiratory tract, emphysema, gastrointestinal diseases: irritable bowel syndrome, intestinal inflammatory disorders, ulcers, diarrhoea, urinary incontinence and inflammation of the bladder.

The use of the compounds according to the invention, in the form of the base, pharmaceutically acceptable acid addition salt, hydrate or solvate, for the preparation of a medicinal product for treating the pathologies mentioned above forms an integral part of the invention.

Also a subject of the invention are medicinal products which contain a compound of formula (I), or a pharmaceutically acceptable acid addition salt or hydrate or solvate of the compound of formula (I). These medicinal products are used in therapy, in particular in the treatment of the pathologies mentioned above.

According to another of its aspects, the present invention relates to pharmaceutical compositions containing as the active principle at least one compound according to the invention. These pharmaceutical compositions contain an effective dose of a compound according to the invention, or a pharmaceutically acceptable acid addition salt, hydrate or solvate of the said compound, and possibly one or more pharmaceutically acceptable excipients.

The said excipients are selected, depending on the pharmaceutical form and the desired administration form, from the usual excipients known to the person skilled in the art.

In the pharmaceutical compositions of the present invention for oral, sublingual, subcutaneous, intramuscular, intravenous, topical, local, intra-thecal, intranasal, transdermal, pulmonary, ocular or rectal administration, the active principle of formula (I) above, or the possible acid addition salt, solvate or hydrate thereof, can be administered to animals and human beings in a unit administration form, mixed with standard pharmaceutical excipients, for the prophylaxis or treatment of the above disorders or diseases.

The appropriate unit administration forms comprise oral forms such as tablets, soft or hard gel capsules, powders, granules, chewing gums and oral solutions or suspensions, sublingual, buccal, intratracheal, intraocular, intranasal administration forms, forms for administration by inhalation, subcutaneous, intramuscular or intravenous administration forms and rectal or vaginal administration forms. For topical administration, the compounds according to the invention may be used in creams, ointments or lotions.

By way of example, a unit administration form of a compound according to the invention in the form of a tablet can comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow daily administration of 0.01 to 20 mg of active principle per kg of body weight, depending on the presentation form.

There may be particular cases in which higher or lower dosages are suitable, and such dosages also form part of the invention. According to normal practice, the dosage appropriate for each patient is determined by the doctor depending on the mode of administration and the weight and response of the said patient.

According to another of its aspects, the invention also relates to a method for treating the pathologies mentioned above which comprises the administration of an effective dose of a compound according to the invention, or one of the pharmaceutically acceptable acid addition salts thereof or a solvate or a hydrate of the said compound.

The invention claimed is:
1. A compound corresponding to the formula (I):

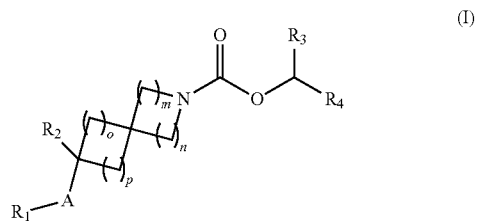

(I)

in which $R_2$ represents a hydrogen or fluorine atom or a hydroxyl, cyano, trifluoromethyl, $C_{1-6}$ alkyl, $C_{1-6}$ alkoxy or $NR_8R_9$ group;

m, n, o and p independently of one another represent a number ranging from 0 to 3;

it being understood that $2 < m+n < 5$ and that $2 < o+p < 5$;

A represents a covalent bond, an oxygen atom, a $C_{1-6}$ alkylene group or an —O—$C_{1-6}$ alkylene group in which the end represented by an oxygen atom is linked to the group $R_1$ and the end represented by an alkylene group is linked to the carbon of the bicyclic system;

$R_1$ represents a group $R_5$ optionally substituted with one or more groups $R_6$ and/or $R_7$;

$R_5$ represents a group selected from a phenyl, pyridinyl, pyridazinyl, pyrimidinyl, pyrazinyl, triazinyl, naphthalenyl, quinolinyl, isoquinolinyl, phthalazinyl, quinazolinyl, quinoxalinyl, cinnolinyl or naphthyridinyl group;

$R_6$ represents a halogen atom, a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, NR$_8$CO$_2$R$_9$, NR$_8$SO$_2$R$_9$, NR$_8$SO$_2$NR$_8$R$_9$, COR$_8$, CO$_2$R$_8$, CONR$_8$R$_9$, SO$_2$R$_8$, SO$_2$NR$_8$R$_9$ or —O—(C$_{1-3}$-alkylene)-O— group;

R$_7$ represents a group selected from a phenyl, pyridinyl, pyridazinyl, pyrimidinyl, pyrazinyl or triazinyl group, the group or group(s) R$_7$ possibly being substituted with one or more groups R$_6$ which are identical to or different from one other;

R$_3$ represents a hydrogen or fluorine atom, a C$_{1-6}$-alkyl group or a trifluoromethyl group;

R$_4$ represents a 5-membered heterocycle selected from a furanyl, pyrrolyl, thienyl, thiazolyl, isothiazolyl, oxazolyl, isoxazolyl, pyrazolyl, oxadiazolyl, thiadiazolyl, imidazolyl, triazolyl or tetrazoyl group;

this heterocycle optionally being substituted with one or more substituents selected from a halogen atom, a C$_{1-6}$-alkyl, C$_{1-6}$-haloalkyl, C$_{3-7}$-cycloalkyl, C$_{3-7}$-cycloalkyl-C$_{1-3}$-alkylene, C$_{1-6}$-haloalkoxy, cyano, NR$_8$R$_9$, NR$_8$COR$_9$, NR$_8$CO$_2$R$_9$, NR$_8$SO$_2$R$_9$, NR$_8$SO$_2$NR$_8$R$_9$, COR$_8$, CO$_2$R$_8$, CONR$_8$R$_9$, CON(R$_8$) (C$_{1-3}$-alkylene-NR$_{10}$R$_{11}$), SO$_2$R$_8$, SO$_2$NR$_8$R$_9$, or —O—(C$_{1-3}$-alkylene)-O group;

R$_8$ and R$_9$ independently of each other represent a hydrogen atom or a C$_{1-6}$-alkyl group;

or with the atom or atoms which bear them form, in the case of NR$_8$R$_9$, a ring selected from the azetidine, pyrrolidine, piperidine, morpholine, thio-morpholine, azepine, oxazepine or piperazine rings, this ring possibly being substituted with a C$_{1-6}$-alkyl or benzyl group;

in the case of NR$_8$COR$_9$, a lactam ring; in the case of NR$_8$CO$_2$R$_9$, an oxazolidinone, oxazinone or oxazepinone ring; in the case of NR$_8$SO$_2$R$_9$, a sultam ring; and in the case of NR$_8$SO$_2$NR$_8$R$_9$, a thiazolidine dioxide or thiadiazinane dioxide ring; and R$_{10}$ and R$_{11}$ independently of one another represent a hydrogen atom or a C$_{1-6}$-alkyl group;

in the form of a base or an acid addition salt and stereoisomers, enantiomers, diastereoisomers, and mixtures thereof.

2. The compound of Claim 1, wherein R$_2$ represents a hydrogen atom;

in the form of a base or an acid addition salt and stereoisomers, enantiomers, diastereoisomers, and mixtures thereof.

3. The compound of Claim 1, wherein m, n, o and p have the value 1, or else p and o have the value 1, and n and m have the value 2, or else n, o and p have the value 1 and m has the value 2;

in the form of a base or an acid addition salt and stereoisomers, enantiomers, diastereoisomers, and mixtures thereof.

4. The compound of claim 1, wherein A represents an oxygen atom, in the form of a base or an acid addition salt and stereoisomers, enantiomers, diastereoisomers, and mixtures thereof.

5. The compound of claim 1, wherein R$_1$ represents a group R$_5$, unsubstituted or substituted with one or more groups R$_6$ and/or R$_7$;

R$_5$ represents a phenyl, naphthalenyl or isoquinolinyl group;

R$_6$ represents a halogen atom, more particularly a fluorine or chlorine atom, or a C$_{1-6}$-haloalkyl, more particularly trifluoromethyl, group or a C$_{1-6}$-alkoxy group, more particularly an ethoxy group; and R$_7$ represents a phenyl which may be substituted with one or more groups R$_6$ which are identical to or different from one another, in the form of a base or an acid addition salt and stereoisomers, enantiomers, diastereoisomers, and mixtures thereof.

6. The compound of claim 1, wherein R$_3$ represents a hydrogen atom, in the form of a base or an acid addition salt and stereoisomers, enantiomers, diastereoisomers, and mixtures thereof.

7. The compound of claim 1, wherein R$_4$ represents a group selected from a thiazolyl, triazolyl, oxazolyl or isoxazolyl, this group being unsubstituted or substituted with one or more C$_{1-6}$-alkyl or CONR$_8$R$_9$ groups, and R$_8$ and R$_9$ independently of one another represent a hydrogen atom or a C$_{1-6}$-alkyl group, in the form of a base or an acid addition salt and stereoisomers, enantiomers, diastereoisomers, and mixtures thereof.

8. The compound of claim 1 selected from:

Thiazol-4-ylmethyl 2-(4-chlorophenoxy)-7-aza-spiro-[3.5]nonane-7-carboxylate;

2-methyl-2H-[1,2,4]-triazol-3-ylmethyl 2-(4-chloro-phenoxy)-7-aza-spiro[3.5]nonane-7-carboxylate and the hydrochloride thereof;

3-methylcarbamoyl-isoxazol-5-ylmethyl 2-(4-chlorophenoxy)-7-aza-spiro[3.5]nonane-7-carboxylate;

3-carbamoyl-isoxazol-5-ylmethyl 2-(4-chlorophenoxy)-7-aza-spiro[3.5]nonane-7-carboxylate;

3-methylcarbamoyl-isoxazol-5-ylmethyl 2-(3-trifluoromethylphenoxy)-7-aza-spiro[3.5]nonane-7-carboxylate;

3-carbamoyl-isoxazol-5-ylmethyl 2-(3-trifluoromethylphenoxy)-7-aza-spiro[3.5]nonane-7-carboxylate;

3-methylcarbamoyl-isoxazol-5-ylmethyl 2-(4'-fluoro-biphenyl-3-yloxy)-7-aza-spiro[3.5]nonane-7-carboxylate;

3-methylcarbamoyl-isoxazol-5-ylmethyl 2-(7-ethoxynaphthalen-2-yloxy)-7-aza-spiro[3.5]nonane-7-carboxylate;

3-carbamoyl-isoxazol-5-ylmethyl 2-(3-trifluoromethylphenoxy)-6-aza-spiro[3.4]octane-6-carboxylate and the hydrochloride thereof;

3-carbamoyl-isoxazol-5-ylmethyl 2-(3-trifluoromethylphenoxy)-6-aza-spiro[3.4]octane-6-carboxylate;

3-carbamoyl-isoxazol-5-ylmethyl 2-(3-trifluoromethylphenoxy)-6-aza-spiro[3.4]octane-6-carboxylate;

3-carbamoyl-isoxazol-5-ylmethyl 2-(4'-fluorobiphenyl-3-yloxy)-7-aza-spiro[3.5]nonane-7-carboxylate;

3-carbamoyl-isoxazol-5-ylmethyl 2-(7-ethoxynaphthalen-2-yloxy)-7-aza-spiro[3.5]nonane-7-carboxylate;

4-carbamoyl-oxazol-2-ylmethyl 2-(3-trifluoromethylphenoxy)-6-azo-spiro[3.4]octane-6-carboxylate;

4-methylcarbamoyl-oxazol-2-ylmethyl 2-(3-trifluoro-methylphenoxy)-6-aza-spiro[3.4]octane-6-carboxylate;

3-carbamoyl-isoxazol-5-ylmethyl 2-(4-chloronaphthalen-1-yloxy)-7-aza-spiro[3.5]nonane-7-carboxylate;

3-methylcarbamoyl-isoxazol-5-ylmethyl 2-(4-chloronaphthalen-1-yloxy)-7-aza-spiro[3.5]nonane-7-carboxylate;

3-carbamoyl-isoxazol-5-ylmethyl 2-(4'-fluorobiphenyl-4-yloxy)-7-aza-spiro[3.5]nonane-7-carboxylate;

3-methylcarbamoyl-isoxazol-5-ylmethyl 2-(4'-fluoro-biphenyl-4-yloxy)-7-aza-spiro[3.5]nonane-7-carboxylate;

4-methylcarbamoyl-thiazol-7-ylmethyl 2-(4'-fluoro-biphenyl-3-yloxy)-7-aza-spiro[3.5]nonane-7-carboxylate;

3-methylcarbamoyl-isoxazol-5-ylmethyl 2-(isoquinolin-7-yloxy)-7-aza-spiro[3.5]nonane-7-carboxylate;

3-methylcarbamoyl-isoxazol-5-ylmethyl 2-(4-chloro-3-fluorophenoxy)-7-aza-spiro[3.5]nonane-7-carboxylate;
3-methylcarbamoyl-isoxazol-5-ylmethyl 6-(4-chloro-3-fluorophenoxy)-2-aza-spiro[3.3]heptane-2-carboxylate;
3-carbamoyl-isoxazol-5-ylmethyl 6-(4-chloro-3-fluorophenoxy)-2-aza-spiro[3.3]heptane-2-carboxylate;
3-methylcarbamoyl-isoxazol-5-ylmethyl 6-(4'-fluoro-biphenyl-4-yloxy)-2-aza-spiro[3.3]heptane-2-carboxylate;
3-carbamoyl-isoxazol-5-ylmethyl 2-(4-chloro-3-fluorophenoxy)-6-aza-spiro[3.4]octane-6-carboxylate;
3-methylcarbamoyl-isoxazol-5-ylmethyl 2-(4-chlorophenoxy)-6-aza-spiro[3.4]octane-6-carboxylate;
3-carbamoyl-isoxazol-5-ylmethyl 2-(4'-fluorobiphenyl-4-yloxy)-6-aza-spiro[3.4]octane-6-carboxylate;
3-methylcarbamoyl-isoxazol-5-ylmethyl 2-(4'-fluoro-biphenyl-4-yloxy)-6-aza-spiro[3.4]octane-6-carboxylate;
3-carbamoyl-isoxazol-5-ylmethyl 2-(4-chloronaphthalen-1-yloxy)-6-aza-spiro[3.4]octane-6-carboxylate;
3-methylcarbamoyl-isoxazol-5-ylmethyl 2-(4-chloronaphthalen-1-yloxy)-6-aza-spiro[3.4]octane-6-carboxylate;
3-methylcarbamoyl-isoxazol-5-ylmethyl 2-(4'-fluoro-biphenyl-4-yloxy)-6-aza-spiro[3.4]octane-6-carboxylate;
3-methylcarbamoyl-isoxazol-5-ylmethyl 2-(4'-fluoro-biphenyl-4-yloxy)-6-aza-spiro[3.4]octane-6-carboxylate;
in the form of a base or an acid addition salt and stereoisomers, enantiomers, diastereoisomers, and mixtures thereof.

9. A process for preparing the compound of claim 1, comprising reacting an amine of general formula (II),

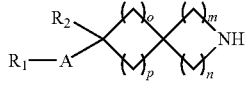
(II)

in which A, $R_1$, $R_2$, m, n, o and p are as defined in the general formula (I) according to claim 1, with a carbonate of general formula (III),

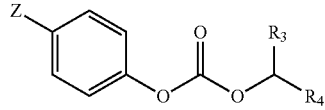
(III)

in which Z represents a hydrogen atom or a nitro group, $R_3$ and $R_4$ are as defined in the general formula (I) according to claim 1,
in the presence of a base, in a solvent at a temperature lying between ambient temperature and the reflux temperature of the solvent.

10. A process for preparing the compound of claim 1, comprising reacting a compound of general formula (Ia)

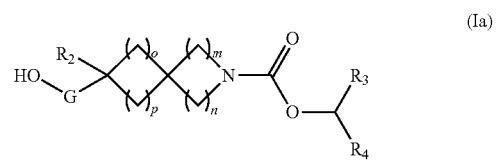
(Ia)

in which $R_2$, $R_3$, $R_4$, m, n, o and p are as defined in the general formula (I) according to claim 1 and G represents a part of the group A as defined in the general formula (I) namely either a covalent bond or the $C_6$-alkylene part of the $-O-C_{1-6}$-alkylene group;
with either an alcohol compound of general formula $R_1OH$ (IV), in which $R_1$ is as defined in the general formula (I) according to claim 1, using the Mitsunobu reaction conditions;
or with a halogenated compound of general formula $R_1X$ (IVa) in which $R_1$ is as defined in the general formula (I) according to claim 1, and X represents a fluorine, chlorine, bromine or iodine atom using aromatic or heteroaromatic nucleophilic substitution, or O-aryl-ation or Buchwald O-heteroarylation reactions.

11. A process for preparing the compound of claim 1, in which $R_1$ represents a group $R_5$ substituted in particular with a group $R_6$ of the $C_{1-6}$-alkyl, $C_{3-7}$-cycloalkyl or $C_{3-7}$-cycloalkyl-$C_3$-alkylene type, or with a group $R_7$ as defined in the general formula (I) according to claim 1, comprising performing a coupling reaction, catalysed by means of a transition metal, on the compound of general formula (Ib),

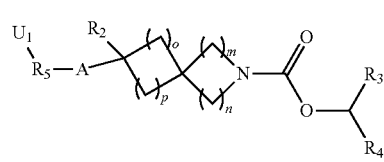
(Ib)

in which A, $R_2$, $R_3$, $R_4$, $R_5$, m, n, o and p are as defined in the general formula (I) according to claim 1 and $U_1$ represents a chlorine, bromine or iodine atom or a triflate group, $U_1$ being in the position where it is desired to introduce the group $R_6$ or $R_7$:
either by a Suzuki type reaction, for example by means of an alkyl, cycloalkyl, aryl or heteroaryl boronic acid,
or by a Stille type reaction, for example using an aryl or heteroaryl tri-alkyltin compound
or by a Negishi type reaction, using an alkyl, cycloalkyl, aryl or heteroaryl halide zincate compound.

12. A pharmaceutical composition comprising the compound of claim 1, in the form of a base or an acid addition salt and stereoisomers, enantiomers, diastereoisomers, and mixtures thereof to a pharmaceutically acceptable acid.

13. The pharmaceutical composition of claim 12, comprising one or more pharmaceutically acceptable excipients.

* * * * *

UNITED STATES PATENT AND TRADEMARK OFFICE
CERTIFICATE OF CORRECTION

PATENT NO. : 8,394,787 B2
APPLICATION NO. : 13/320199
DATED : March 12, 2013
INVENTOR(S) : Abouabdellah et al.

It is certified that error appears in the above-identified patent and that said Letters Patent is hereby corrected as shown below:

On the title page item [57]:

Line 5 replace "$m+n \leqq 7$" with --$2 \leq m+n \leq 5$--;

Line 5 replace "$o+p \leqq 7$" with --$2 \leq o+p \leq 5$--.

In the Specification:

Column 1, line 27; replace "trifluoromethyl, $C_{1-6}$-alkoxy" with --trifluoromethyl, $C_{1-6}$-alkyl, $C_{1-6}$-alkoxy--;

Column 1, line 30; replace "$2 \leqq m+n \leqq 5$" with --$2 \leq m+n \leq 5$--;

Column 1, line 30; replace "$2 \leqq o+p \leqq 5$" with --$2 \leq o+p \leq 5$--.

In the Claims:

Column 44, claim 1, line 47-48; replace "$C_{1,6}$ alkyl, $C_{1-6}$ alkoxy" with --$C_{1-6}$ alkyl, $C_{1-6}$ alkoxy --;

Column 44, claim 1, line 51; replace "$2<m+n<5$" with --$2 \leq m+n \leq 5$--;

Column 44, claim 1, line 51; replace "$2<o+p<5$" with --$2 \leq o+p \leq 5$--;

Column 44, claim 1, line 52-53; replace "$C_{1,6}$ alkylene" with --$C_{1-6}$ alkylene--;

Signed and Sealed this
Eighteenth Day of August, 2015

Michelle K. Lee
*Director of the United States Patent and Trademark Office*

CERTIFICATE OF CORRECTION (continued)
U.S. Pat. No. 8,394,787 B2

Column 44, claim 1, line 53; replace " -O-$C_{1,6}$ alkylene" with -- -O-$C_{1-6}$ alkylene--;

Column 44, claim 1, line 64; replace "$C_{1-6}$-thioalkyl," with --$C_{1-6}$-thioalkyl,--;

Column 45, claim 1, line 21-22; replace "CON($R_8$) ($C_{1-3}$-alkylene-$NR_{IO}R_{II}$), $SO_2R_s$," with --CON($R_8$) ($C_{1-3}$-alkylene-$NR_{10}R_{11}$), $SO_2R_8$,--;

Column 45, claim 4, line 53; replace "claim" with --Claim--;

Column 45, claim 5, line 57; replace "claim" with --Claim--;

Column 46, claim 6, line 4; replace "claim" with --Claim--;

Column 46, claim 7, line: 8; replace "claim" with --Claim--;

Column 46, claim 8, line 16; replace "claim" with --Claim--;

Column 47, claim 9, line 31; replace "claim" with --Claim--;

Column 47, claim 9, line 41; replace "claim" with --Claim--;

Column 47, claim 9, line 54; replace "claim" with --Claim--;

Column 47, claim 10, line 58; replace "claim" with --Claim--;

Column 48, claim 10, line 10; replace "claim" with --Claim--;

Column 48, claim 10, line 13; replace "$C_6$-alkylene" with --$C_{1-6}$-alkylene--;

Column 48, claim 10, line 16; replace "claim" with --Claim--;

Column 48, claim 10, line 20; replace "claim" with --Claim--;

Column 48, claim 11, line 24; replace "claim" with --Claim--;

Column 48, claim 11, line 27; replace "cloalkyl-$C_3$-alkylene" with --cloalkyl-$C_{1-3}$-alkylene--;

Column 48, claim 11, line 28; replace "claim" with --Claim--;

Column 48, claim 11, line 42; replace "claim" with --Claim--;

Column 48, claim 12, line 53; replace "claim" with --Claim--;

Column 48, claim 13, line 56; replace "claim" with --Claim--.